(12) United States Patent
Tian et al.

(10) Patent No.: US 10,292,986 B2
(45) Date of Patent: May 21, 2019

(54) METHODS FOR TREATING EPITHELIAN MESENCHYMAL TRANSITION RELATED DISEASES

(71) Applicants: Bing Tian, Galveston, TX (US); Allan Brasier, Galveston, TX (US)

(72) Inventors: Bing Tian, Galveston, TX (US); Allan Brasier, Galveston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/144,286

(22) Filed: May 2, 2016

(65) Prior Publication Data

US 2016/0317548 A1    Nov. 3, 2016

Related U.S. Application Data

(60) Provisional application No. 62/155,950, filed on May 1, 2015.

(51) Int. Cl.
*A61K 31/551* (2006.01)
*A61K 45/06* (2006.01)

(52) U.S. Cl.
CPC ............ *A61K 31/551* (2013.01); *A61K 45/06* (2013.01)

(58) Field of Classification Search
None
See application file for complete search history.

(56) References Cited

U.S. PATENT DOCUMENTS 8,357,673 B2 * 1/2013 Cankar ................ C07D 231/38
514/150

OTHER PUBLICATIONS

Tian, X. et al., Am. J. Pathol. 2013, vol. 183, pp. 470-479.*
Duechs, M. et al PLOS ONE 2014 vol. 9, pp. 1-1.*
May, RD et al., Br. J. Pharmacol 2012 vol. 166, pp. 177-193.*
Jackson, R. et al., BioDiscovery 2013 vol. 7, pp. 1-11.*
Khan, Y. et al., PLOS One 2014 vol. 9, pp. 1-17.*
Perry, M. et al., J. Biol Chem. 2015, vol. 290, pp. 9111-9121.*
Durham, A. et al Eur. Resp. J. 2014 vol. 42 Suppl 57.*
Alexopoulou et al., "Recognition of double-stranded RNA and activation of NF-kappaB by Toll-like receptor 3," *Nature*, vol. 413, No. 6857, 2001, pp. 732-738.
Bisgrove et al., "Conserved P-TEFb-interacting domain of BRD4 inhibits HIV transcription," *PNAS*, vol. 104, No. 34, 2007, pp. 13690-13695.
Brasier et al., "RelA Ser276 Phosphorylation-Coupled Lys310 Acetylation Controls Transcriptional Elongation of Inflammatory Cytokines in Respiratory Syncytial Virus Infection," *J. Virol.* vol. 85, No. 22, 2011, pp. 11752-11769.

Brown et al., "NF-kB Directs Dynamic Super Enhancer Formation in Inflammation and Atherogenesis," *Mol Cell*, vol. 56, No. 2, 2014, pp. 219-231.
Burke et al., "BMS-345541 is a Highly Selective Inhibitor of IkB Kinase That Binds at an Allosteric Site of the Enzyme and Blocks NF-kB-dependent Transcription in Mice," *J. Biol. Chem.*, vol. 278, No. 3, 2003, pp. 1450-1456.
De Boer et al., "Altered expression of epithelial junctional proteins in atopic asthma: possible role in inflammation," *Can J Physiol Pharmacol*, vol. 86, No. 3, 2008, pp. 105-112.
Filippakopoulos et al., "Selective inhibition of BET bromodomains," *Nature*, vol. 468, No. 7327, 2010, pp. 1067-1073.
Fitzgerald et al., "LPS-TLR4 Signaling IRF-3/7 and Nf-kB Involved the Toll Adapters TRAM and TRIF," *J. Exp. Med.*, vol. 198, No. 7, 2003, pp. 1043-1055.
Huang et al., "Junin Virus Infection Activates the Type I Interferon Pathway in a RIG-I-Dependent Manner," *PLoS. Negl. Trop. Dis.*, vol. 6, No. 5, 2012, e1659, pp. 1-10.
Huang et. al., *J Cell Sci*, 2012, 125(19):4417-22.
Huber et al., "Epithelial-mesenchymal transition: NF-κB takes center stage," *Cell Cycle*, vol. 3, No. 12, 2004, pp. 1477-1480.
Huber et al., *J Clin Invest*, 2004, 114(4):569-581.
Ijaz et al., *World Allergy Organ J*, 2014, 7(1):13.
Jang et al., 2005, *Mol. Cell*. 19:523-34.
Kalita et al., 2013, *Biomed. Res. Int.* 2013:505864.
Kalluri and Weinberg, *J Clin Invest*, 2009, 119(6):1420-28.
Kaltenborn et al., *Hum Mol Genet*, 2012, 21(12):2793-806.
Kanno et al., *Nat Struct Mol Biol*, 2014, 21(12):1047-57.
Kim HJ et al., *Mol Cell Biol*, 2007, 27(8), 3165-3175.
Korkaya et al., 2012, *Mol. Cell*. 47:570-84.
Lambrecht et al., "The airway epithelium in asthma," *Nat Med*, vol. 18, No. 5, 2012, pp. 684-692.
Li et al., *Cancer Res*, 2012, 72(5):1290-1300.
Liu et al., 2007, *J. Virol.* 81:1401-11.
McDonald et al., 2011, *Nat. Struct. Mol. Biol.* 18:867-74.
Nowak et al., 2005, *Biotechniques*. 39:715-25.
Nowak et al., 2008, *Mol. Cell. Biol.* 28:3623-38.
Ramirez et al., "Immortalization of Human Bronchial Epithelial Cells in the Absence of Viral Oncoproteins," *Cancer Res*, 2004, vol. 64, No. 24, 2004, pp. 9027-9034.
Tian et al., 2005, *J. Biol. Chem.* 280:17435-48.
Tian et al., 2012, *Methods. Mol. Biol.* 809:105-20.
Tian et al., 2015, *BMC. Genomics*. 16:529.
Tian et al., *J Virol*, 2013, 87(12):7075-92.

(Continued)

*Primary Examiner* — Heidi Reese
(74) *Attorney, Agent, or Firm* — Norton Rose Fulbright US LLP

(57) ABSTRACT

Certain embodiments are directed to methods of treating chronic lung diseases in a subject comprising administering to a subject diagnosed with, exhibiting symptoms of, or at risk of developing a chronic lung disease a therapeutically effective amount of a BRD4 inhibitor or a CDK9 inhibitor to the subject.

4 Claims, 32 Drawing Sheets
Specification includes a Sequence Listing.

(56) References Cited

OTHER PUBLICATIONS

Wu et al., "The Double Bromodomain-containing Chromatin Adaptor Brd4 and Transcriptional Regulation," *J Biol Chem*, vol. 282, No. 18, 2007, pp. 13141-13145.
Xu and Vakoc, *Trends Cell Biol*, 2014, 24(11):615-16.
Yang et al., "The 7SK small nuclear RNA inhibits the CDK9/cyclin T1 kinase to control transcription," *Nature*, vol. 414, No. 6861, 2001, pp. 317-322.
Zhao et al., 2011, *Mol. Cell. Proteomics*. 10:M111.
Zhao et al., 2013, *Mol. Cell. Proteomics*. 12:1513-29.

* cited by examiner

A

A

D

A

B

C

METHODS FOR TREATING EPITHELIAN MESENCHYMAL TRANSITION RELATED DISEASES

This Application claims priority to U.S. Provisional Patent Application Ser. No. 62/155,950 filed May 1, 2015, which is incorporated herein by reference in its entirety.

STATEMENT REGARDING FEDERALLY FUNDED RESEARCH

This invention was made with government support under P01AI062885 awarded by the National Institute of Allergy and Infectious Diseases. The government has certain rights in the invention.

BACKGROUND

Chronic epithelial injury is a hallmark of inflammatory lung disease. Mucosal repair is mediated by a cell state transition of normal epithelial cells, known as Type II epithelial-mesenchymal transition (EMT), responsible for myofibroblast expansion, epithelial trans-differentiation, and subepithelial fibrosis. Currently, very little is known about the factors initiating type II EMT.

Chronic lung disease is the second largest cause of mortality worldwide (Durham et al., *Biochim Biophys Acta*, 2011, 1810(11):1103-09). A pathological hallmark of asthma is disruption of the epithelial cell barrier (Lambrecht and Hammad, *Nat Med*, 2012, 18(5):684-92). Upon exposure to respiratory viruses or environmental oxidants, resident epithelial cells undergo epigenetic and phenotypic changes to produce pro-inflammatory mediators, express extracellular matrix, and expand the myofibroblast population (Ijaz et al., *World Allergy Organ J*, 2014, 7(1):13). These phenotypic changes are associated with enhanced motility, resistance to reactive oxygen species (ROS) and expression of fibrotic genes, processes together known as Type II EMT (Kalluri and Weinberg, *J Clin Invest*, 2009, 119(6):1420-28). Although important in tissue repair, unregulated EMT plays a critical cellular role in the progression of chronic human pulmonary fibrotic diseases, diseases including atopic asthma, chronic obstructive pulmonary disease (COPD), and idiopathic pulmonary fibrosis (IPF) (de Boer et al., *Can J Physiol Pharmacol*, 2008, 86(3):105-12). EMT has also recently been observed in chronic airway disease associated with cystic fibrosis or severe respiratory syncytial virus (RSV), a risk factor for the development of allergic asthma later in life (Kaltenborn et al., *Hum Mol Genet*, 2012, 21(12):2793-806). All of this evidence suggests that EMT plays important roles in the pathogenesis of airway remodeling in response to environmental stressors.

There remains a need for additional methods and compositions for treating EMT related to fibrosis, asthma, or COPD.

SUMMARY

Certain embodiments are directed to methods of treating chronic lung diseases in a subject comprising administering to a subject diagnosed with, exhibiting symptoms of, or at risk of developing a chronic lung disease a therapeutically effective amount of a BRD4 inhibitor or a CDK9 inhibitor to the subject. In certain aspects the chronic lung disease comprises fibrosis of the lung. In a further aspect the fibrotic lung disease is fibrotic chronic obstructive pulmonary disease (COPD) or severe, i.e., steroid-resistant, asthma. The methods described herein can further comprise administering a second active agent, e.g., an anti-inflammatory agent.

Other embodiments are directed to methods of treating viral bronchiolitis in a subject comprising administering to a subject diagnosed with, exhibiting symptoms of, or at risk of developing viral bronchiolitis a therapeutically effective amount of a BRD4 inhibitor or a CDK9 inhibitor to the subject.

Certain embodiments of the invention are directed to methods of treating chronic obstructive pulmonary disease (COPD) in a subject diagnosed with, exhibiting symptoms of, or at risk of developing COPD by administering a therapeutically effective amount of a BRD4 inhibitor.

As used herein, a "risk" of developing a disease is based on the subject's medical, personal, and/or family history. In particular, current or previous smoking (most notably cigarettes, but also other nicotine or non-nicotine, e.g., marijuana, products) indicate a risk of developing lung diseases like COPD, but risk factors also include, but are not limited to exposure to smoke or other environmental hazards (e.g., mining or textile industry hazards, fumes, air pollution), genetic susceptibility, autoimmune disease, and bronchial hyperresponsiveness. A subject may also be one that exhibits one or more symptoms of lung disease including, but not limited to: chronic cough, sputum production, dyspnea (shortness of breath), rhonchi (rattling breathing sounds), and airway limitation on pulmonary function testing.

In certain aspects, the BRD4 inhibitor is administered to the patient as a prodrug. Typically, a prodrug is an inactive or less active form of a drug that is metabolized or converted in vivo to an active or more active form.

In certain aspects BRD4 inhibitor agent is administered at a dose of between 50, 100, 150, 200, 250, 300 to 250, 300, 350, 400, 450, 500, 550, 600 mg/day, including all values and ranges there between. In certain aspects 50, 100, 150, 200, 250, 300, 350, 400, 450, 500, 550, or 600 mg of BRD4 inhibitor is administered. In a further aspect the dose of BRD4 inhibitor agent is administered in one dose or in multiple doses over 0.5, 1, 2, 3, 4, 5, 6, 7, 8, 9, or 10 minutes, hours or days. The BRD4 inhibitor can be administered by any route, including orally, endoscopically, intratracheally, intrabronchially, intravenously, intralesionally, intramuscularly, intraperitoneally, percutaneously, or subcutaneously. In certain aspects the BRD4 is administered orally or by inhalation or instillation, e.g., by inhaler or other aerosol delivery devices.

Certain embodiments of the invention are directed to methods of treating chronic obstructive pulmonary disease (COPD) in a subject diagnosed with, exhibiting symptoms of, or at risk of developing COPD by administering a therapeutically effective amount of a CDK9 inhibitor. As used herein, a "risk" of developing COPD is based on the subject's medical, personal, and/or family history. In particular, current or previous smoking (most notably cigarettes, but also other nicotine or non-nicotine, e.g., marijuana, products) indicate a risk of developing COPD, but risk factors also include, but are not limited to exposure to smoke or other environmental hazards (e.g., mining or textile industry hazards, fumes, air pollution), genetic susceptibility, autoimmune disease, and bronchial hyperresponsiveness. A subject may also be one that exhibits one or more symptoms of COPD including, but not limited to: chronic cough, sputum production, dyspnea (shortness of breath), rhonchi (rattling breathing sounds), and airway limitation on pulmonary function testing.

In certain aspects, the CDK9 inhibitor is administered to the patient as a prodrug. Typically, a prodrug is an inactive or less active form of a drug that is metabolized or converted in vivo to an active or more active form.

In certain aspects CDK9 inhibitor agent is administered at a dose of between 50, 100, 150, 200, 250, 300 to 250, 300, 350, 400, 450, 500, 550, 600 mg/day, including all values and ranges there between. In certain aspects 50, 100, 150, 200, 250, 300, 350, 400, 450, 500, 550, or 600 mg of CDK9 inhibitor is administered. In a further aspect the dose of CDK9 inhibitor agent is administered in one dose or in multiple doses over 0.5, 1, 2, 3, 4, 5, 6, 7, 8, 9, or 10 minutes, hours or days. The CDK9 inhibitor can be administered by any route, including orally, endoscopically, intratracheally, intrabronchially, intravenously, intralesionally, intramuscularly, intraperitoneally, percutaneously, or subcutaneously. In certain aspects the CDK9 is administered orally or by inhalation or instillation, e.g., by inhaler or other aerosol delivery devices.

As used herein, a kinase "inhibitor" refers to any compound capable of downregulating, decreasing, suppressing or otherwise regulating the amount and/or activity of a kinase Inhibition of these kinases can be achieved by any of a variety of mechanisms known in the art, including, but not limited to binding directly to the kinase polypeptide, denaturing or otherwise inactivating the kinase, or inhibiting the expression of the gene (e.g., transcription to mRNA, translation to a nascent polypeptide, and/or final polypeptide modifications to a mature protein), which encodes the kinase. Generally, kinase inhibitors may be proteins, polypeptides, nucleic acids, small molecules, or other chemical moieties.

As used herein the term "inhibiting" or "inhibition" refers to the ability of a compound to downregulate, decrease, reduce, suppress, inactivate, or inhibit at least partially the activity of a protein, or the expression of a protein.

The term "BRD4 inhibitor" means accordingly in this context a compound capable of inhibiting the expression and/or activity of "BRD4" defined herein. A BRD4 inhibitor may, for example, interfere with transcription of a BRD4 gene, processing (e.g. splicing, export from the nucleus and the like) of the gene product (e.g. unspliced or partially spliced mRNA) and/or translation of the gene product (e.g. mature mRNA). The BRD4 inhibitor may also interfere with further modification (like phosphorylation) of the polypeptide/protein encoded by the BRD4 gene and thus completely or partially inhibit the activity of the BRD4 protein as described herein above. Furthermore, the BRD4 inhibitor may interfere with interactions of the BRD4 protein with other proteins or nucleic acids. An example of a BRD4 inhibitor is JQ1.

In certain embodiments the BRD4 inhibitor is a peptide, a peptide mimetic, a small molecule, or an inhibitory RNA. The BRD4 inhibitor can be a siRNA or other inhibitory nucleic acid, a carboxylic acid, a hydantoin, a pyridazinone, or a pharmaceutically acceptable derivative thereof.

The term "CDK9 inhibitor" means accordingly in this context a compound capable of inhibiting the expression and/or activity of "CDK9" defined herein. A CDK9 inhibitor may, for example, interfere with transcription of a CDK9 gene, processing (e.g. splicing, export from the nucleus and the like) of the gene product (e.g. unspliced or partially spliced mRNA) and/or translation of the gene product (e.g. mature mRNA). The CDK9 inhibitor may also interfere with further modification (like phosphorylation) of the polypeptide/protein encoded by the CDK9 gene and thus completely or partially inhibit the activity of the CDK9 protein as described herein above. Furthermore, the CDK9 inhibitor may interfere with interactions of the CDK9 protein with other proteins. One example of a CDK9 inhibitor is CAN508, LDC000067, flavopiridol, or seliciclib (aka roscovitine).

In certain embodiments the CDK9 inhibitor is a peptide, a peptide mimetic, a small molecule, or an inhibitory RNA. The CDK9 inhibitor can be a siRNA or other inhibitory nucleic acid, a carboxylic acid, a hydantoin, a pyridazinone, or a pharmaceutically acceptable derivative thereof.

The term "treating" includes treating a physiological cause of disease, treating a condition associated with the disease, and treating one or more symptoms of the disease. Treating includes reducing the severity (including any measurable decrease to complete elimination), reducing the frequency, slowing or stopping the progression of, increasing the time until onset, or preventing the onset of one or more disease symptoms.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1A:
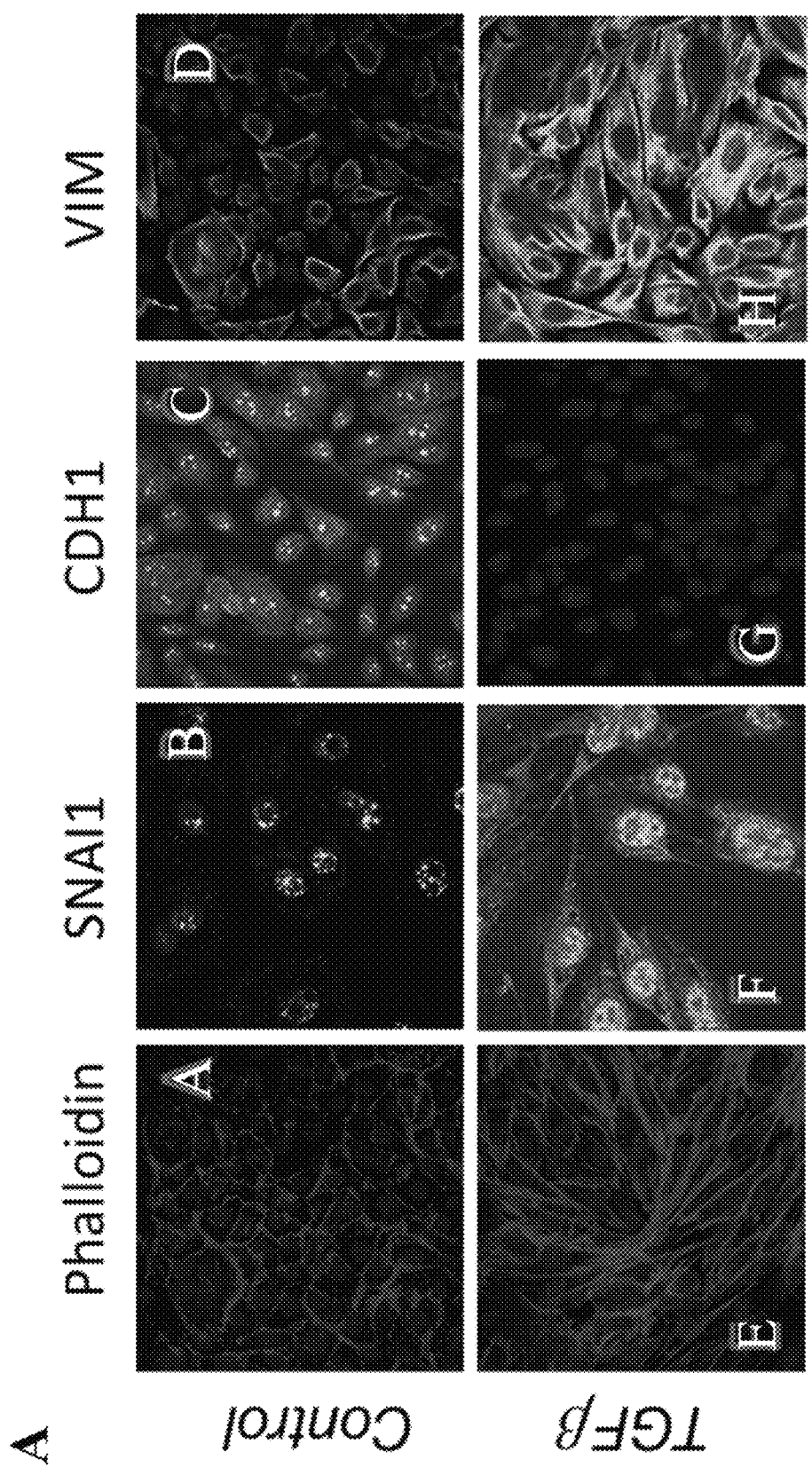
FIG. 1A-1B. TGFβ induces a type II EMT in hSAECs. (A) Confocal images of formation of a Type II EMT in hSAECs. hSAECs were incubated in the absence or presence of TGFβ (10 ng/mL) for 15 days. Cells were stained with Alexa568-conjugated phalloidin (for distribution of F-actin) and DAPI (a nuclear DNA stain). Additionally, cells were incubated with primary antibodies (Abs) for the mesenchymal markers SNAI1 and Vimentin or the epithelial marker E-Cadherin (CDH1), then stained with Alexa Fluor 488-conjugated Goat anti-rabbit IgG, counterstained with DAPI, and imaged to examine these proteins' levels and distributions within hSAECs. (B) TGFβ induces the EMT controlling gene expression in hSAECs. hSAECs were incubated with a time series of TGFβ (10 ng/mL) up to 15 days. Total RNA was reverse-transcribed. The expression of core transcription factors (SNAI1 TWIST1, and ZEB1), mesenchymal markers Vimentin (VIM), collagen 1A (COL1A), and fibronectin (FN1), and the epithelial marker CDH1 were examined by Q-RT-PCR. Shown is the fold-change in mRNA abundance normalized to cyclophilin. ANOVA was performed looking for time differences, followed by Tukey's post hoc test to determine significance. *=$p<0.05$ compared to without TGFβ. Data are the means±S.D. from n=3 independent experiments.

Maintenance of epithelial integrity is critical to normal cellular signaling, pulmonary homeostasis, and response to toxicants and allergen exposures. Epithelial injury releases latent TGFβ, a growth factor sequestered by the extracellular matrix that triggers primary pathways involved in epithelial repair. Liberated TGFβ binds to the extracellular transmembrane serine/threonine kinase, TGFβ receptor type II (TGFβRII), that recruits and phosphorylates TGFβRI to signal through Smad-dependent, "canonical", and Smad-independent, "non-canonical", pathways. In the canonical pathway, phosphorylated Smad2/3 binds to Smad4 and the complex then translocates to the nucleus. The Smad complex regulates components of the core EMT transcriptional regulators, including Snail (SNA1), a zinc finger-containing transcription factor responsible for repressing epithelial cadherin (CDH) and zinc finger E-box binding (ZEB)1, a homeobox protein that upregulates TGFB 1 and Vimentin (VIM). In the non-canonical signaling pathway, downstream PI3K/Akt, Ras small GTPases, Wnt/β-catenin, ERK, p38, and JNK modulate actions of the core EMT regulators. Collectively, the canonical and non-canonical pathways are both required to initiate and maintain EMT.

TGFβ-stimulation induces epithelial cells to undergo transcriptional reprogramming, de-differentiating them from highly specialized epithelial cells to become fibroblast-like cells with stem-cell like characteristics. At the cellular level, TGFβ-induced type II EMT leads to the loss of apical polarity, reduced epithelial cadherin (CDH1) and disruption of epithelial adherens junctions. In addition, type II EMT enables transformed epithelial cells to express α-SMA stress fibers and intermediate filament vimentin (VIM) and to produce extra-cellular matrix through secretion of collagen and fibronectin (FN1) and matrix metalloproteinases (MMPs). In this manner, type II EMT enables epithelial cells to become motile, induce extracellular matrix remodeling, coordinating airway fibrosis, repair, and regeneration.

The coordinate TGFβ response is dramatically affected by inflammation-associated signaling factors, extracellular matrix cues and the presence of oncogenic Ras transformation. Type II EMT also produces complex alterations in the tumor necrosis factor α (TNFα)-nuclear factor κB (NFκB) signal transduction pathway. NFκB is a central mediator of the epithelial inflammatory response to cytokines, ROS, and respiratory viruses. In resting epithelial cells, NFκB dynamically shuttles as an inactive complex bound the ankyrin repeat-containing IκB protein family. In response to activation via the prototypical TNFα-TNFRI pathway, rate-limiting IκB kinases phosphorylate serine residues in the NH2 terminus of IκB within minutes, triggering binding to the E3 ubiquitin ligase, BTRC/βTrCP, and subsequent proteolytic destruction through the 26S proteasome and calpain pathways. Liberated NFκB is then released to be transported into the nucleus through a dynein-dependent active transport pathway to bind high affinity sites in the genome coordinating temporal waves of gene expression.

NFκB/RelA activation is controlled by a two-step process involving liberation from its cytoplasmic inhibitor followed by site-specific phosphorylation at Ser 276 through a family of ROS-sensitive ribosomal S6 kinases (Jamaluddin et al., *Cell Signal*, 2007, 19(7):1419-33). Specifically, phospho-Ser 276 RelA is critical for activation of a subset of highly inducible inflammatory genes by activating transcriptional elongation (Nowak et al., *Mol Cell Biol*, 2008, 28(11):3623-38; Brasier et al., *J Virol* 2011, 85(22):11752-69). In this pathway, phospho-Ser 276 RelA forms a complex with the CDK9 kinase complex, a complex responsible for phosphorylation of Ser2 of the carboxyl terminal domain (CTD) of RNA Pol II, licensing it to produce fully spliced transcripts (Brasier et al., *J Virol* 2011, 85(22):11752-69). NFκB dependent target genes are under a phosphorylation code, with immediate early genes requiring Ser276 phosphorylation coupled to CDK9-mediated transcriptional elongation, whereas IκB/A20 are Ser276 phosphorylation-and CDK9-independent.

Although the role of NFκB in inflammation mediated signaling is well-established, its role in mediating type II EMT is not understood. A biologically relevant model of the TGFβ-inducible type II EMT using immortalized primary hSAECs was established (Kalita et al., Biomed Res Int, 2013). As described herein, the inventors define the role of activated NFκB in the transcriptional reprogramming of EMT regulators during the type II EMT in airway epithelial cells. Activation of the EMT program results in a time dependent expression of the EMT core regulators, SNAI1, ZEB and Twist over 15 d, with coincident expression of NFκB-dependent genes. In contrast to its rapid activation by TNFRI, TGFBR activation of NFκB required 3d suggesting a distinct intracellular signal transduction pathway. TGFβ induced formation of NFκB·BRD4 complex and recruitment of BRD4 to EMT core transcription regulators. Inhibition of BRD4 using small molecule inhibitors or shRNA-mediated knockdown blocked the EMT program and stable assembly of the transcriptional elongation complex. The inventors conclude that NFκB-dependent BRD4 recruitment is a major regulator of TGFβ-induced transcriptional reprogramming in airway epithelial cells, affecting transcriptional elongation to promote and maintain type II EMT formation.

As described herein, the role of activated NFκB-dependent BRD4 recruitment in type II EMT initiation and transcriptional reprogramming in human airway epithelial cells was examined. It was demonstrated that chronic stimulation of TGFβ activated NFκB/RelA signaling in airway epithelial cells through induction of NFκB/Rel translocation and preferential activation of phosphor-Ser276 RelA-dependent immediate early genes. Also, it was found that inhibition of NFκB/RelA resulted in repression of TGF-induced EMT genes. Also, Inhibition of BRD4 blocks TGFβ-induced EMT initiation and expression of EMT core regulatory genes SNAI/1, ZEB, Twist1, and IL-6. During this process, RelA Ser276 phosphorylation is required for BRD4 recruitment. The activated NFκB/RelA recruit BRD4 to the NF-κB binding sites of promoters of EMT genes (SNAIL1/ZEB1/Twist1/IL6) to induce reprogramming of transcriptional elongation complex, resulting overexpression of EMT genes and promoting initiation and maintenance of type II EMT. The results support NFκB-dependent BRD4 recruitment as being a major determinant of type II EMT initiation and transcriptional reprogramming.

The detailed mechanism how NF-κB/RelA controls EMT are incompletely understood. In studies of cancer-associated Type III EMT, NF-κB is required for IGF-induced EMT by directly inducing SNAIL1 (Kim H J et al., *Mol Cell Biol*, 2007, 27(8), 3165-3175). NF-κB has also been shown to upregulate ZEB1/2 and Twist1 (Li et al., *Cancer Res*, 2012, 72(5):1290-1300), explaining, in part, how the IL-1/TNF superfamily of cytokines modulate Type III EMT. In earlier studies, using more precise time series, it was observed that SNAI1 is the earliest upregulated core transcription factor in Type II EMT and whose significant induction precedes that of ZEB1 and Twist1, leading us to suggest that SNAIL1 is an initial trigger of EMT (Kalita et al., *Biomed Res Int.*, 2013, 505864). NF-κB/RelA activation is an early, necessary mediator for TGFβ-induced EMT. This transcription factor is activated by the TGFβ-associated kinase (TAK) pathway, whose actions are upstream of the core EMT regulators SNAIL1 and Twist, making RelA a central mediator of the EMT (Huber et al., *J Clin Invest*, 2004, 114(4): 569-81; Huber et al., *Cell Cycle*, 2004, 3(12):1477-80). As described herein, it was found that activation of NF-κB/RelA is required for initiation of TGFβ-induced core EMT transcription factor and mesenchymal genes based on convergent results from the small molecule IKK kinase inhibitor BMS-345541 (Burke et al., *J Biol Chem*, 2003, 278(3):1450-56). It was found that treatments inhibited TGFβ-induced enhanced mesenchymal gene expression. Furthermore, it was found that RelA Ser 276 phosphorylation is required for activated NFκB/RelA mediated Type II EMT during TGFβ stimulation. All these data indicate NF-κB/RelA activation is a necessary component of the TGFβ-induced type II EMT in hSAECs.

It has been documented that the core EMT transcription factor and SNAIL1, ZEB1, and Twist1, and mesenchymal genes VIM and FN1 are NFκB-dependent that are bound directly in their proximal promoters (Huber et al., *J Clin Invest*, 2004, 114(4):569-581; Kim et al., *Mol Cell Biol*, 2007, 27(8):3165-75; Li et al., *Cancer Res*, 2012, 72(5): 1290-1300; Huber et al., *Cell Cycle*, 2004, 3(12):1477-80). The inventor contemplate that TGFβ-induced the formation of NFκB activated transcription complex RelA/CDK9/BRD4/pPol II Ser2 on the 5' NFκB sites of EMT genes, promoting EMT gene expression and initiating type II EMT. Indeed, it was found that chronic TGFβ treatment induces an active RelA/BRD4/CDK9 complex in nuclei of hSAECs during EMT process. Also, the NFκB signaling pathway was perturbed to examine the recruitment of transcriptional complex assembly to NF-κB binding sites of EMT gene promoters and found that the recruitment of RelA, CDK9, BRD4, and pSer2 Pol II to 5' NFκB site of EMT promoters were significantly attenuated by RelA inhibition. All results support that TGFβ-induced type II EMT initiation and transcriptional reprogramming are mediated by activated NFκB/Rel A.

The bromodomain protein BDR4 is a chromatin remodeling enzyme recognized as one of the most important regulators of immune responses (Filippakopoulos et al., Nature, 2010, 468(7327):1067-73; Xu and Vakoc, *Trends Cell Biol*, 2014, 24(11):615-16; Brown et al., Mol Cell, 2014, 56(2):219-31; Kanno et al., *Nat Struct Mol Biol*, 2014, 21(12):1047-57). The bromodomain and extraterminal domain (BET) family proteins (Wu and Chiang, *J Biol Chem*, 2007, 282(18):13141-45), including BRD2, BRD3, BRD4 and BRDT, contain two bromodomains (BDs) (Filippakopoulos et al., Nature, 2010, 468(7327):1067-1073), Among ubiquitously expressed BET family proteins, BRD4 is unique in that it interacts with P-TEFb through its C-terminal tail (Bisgrove et al., *PNAS USA*, 2007, 104(34): 13690-95). BRD4 is a mammalian bromodomain protein that preferentially binds to acetylated histone H4 (H4-KAc) in living cells (Brasier et al., *J Virol*, 2011, 85(22):11752-69; Jang et al., *Mol Cell*, 2005, 19(4):523-34; Yang et al., Nature, 2001, 414(6861):317-22). Through H4-KAc binding, BRD4 is a critical mediator of transcriptional elongation, functioning to recruit activated CDK9 to the promoter (Jang et al., *Mol Cell*, 2005, 19(4):523-34; Yang et al., Nature, 2001, 414(6861):317-22). Previous studies have demonstrated that RSV infection in the airway epithelium shifts CDK9 into an activated complex by increasing its binding to BRD4 and disrupting the association of CDK9 with its negative regulator 7SK snRNA (Brasier et al., *J Virol*, 2011, 85(22):11752-69; Tian et al., *J Virol*, 2013, 87(12):7075-92). The small-molecule inhibitor JQ1 has recently been identified that can displace BRD4 from histones by competitively binding to its acetylated lysine recognition pocket (Filippakopoulos et al., *Nature*, 2010, 468(7327):1067-73), which provides a powerful tool to probe the role of BRD4 under physiological conditions. Recently, it has been reported that NF-κB coordinates rapid, BRD4-dependent remodeling of proinflammatory super-enhancers in inflammation and atherogenesis. Super enhancer-bound BRD4 coactivates inflammatory genes and chronic treatment of BRD4 inhibitor JQ1 attenuates atherogenic responses and atherosclerosis (Brown et al., *Mol Cell* 2014, 56(2):219-31). This work reveals new principles of enhancer dynamics and insights into the therapeutic modulation of enhancer function with BET bromodomain inhibitors and targeting Brd4 exhibits promising specificity for inflammatory responses in vivo (Brown et al., *Mol Cell*, 2014, 56(2):219-31; Xu and Vakoc, *Trends Cell Biol*, 2014, 24(11): 615-16).

Studies described herein have revealed the dominant role of BRD4 in the initiation and maintenance of epithelial type II EMT. It was found that BRD4 inhibition blocks TGFβ-induced EMT morphology and decreases protein levels and the cellular distribution pattern of EMT genes induced by chronic TGFβ while it restore the protein levels and the cellular distribution pattern of the epithelial marker E-Cadherin in TGFβ treated hSAECs. It was also found that both BRD4 inhibitor JQ1 and BRD4 siRNA silencing significantly inhibited TGFβ-induced enhanced mesenchymal gene expression. Furthermore, the recruitment of components of NFκB transcription complex RelA, CDK9, BRD4, and pSer2 Pol II to 5' NFκB site of EMT promoters were disrupted by BRD4 inhibition. The results support NFκB-dependent BRD4 recruitment as a major determinant of type II EMT initiation and transcriptional reprogramming.

Persistent EMT is associated with severe refractory asthma and chronic airway remodeling, resulting in a progressive decline in pulmonary function (Ijaz et al., *World Allergy Organ J*, 2014, 7(1):13; de Boer et al., *Can J Physiol Pharmacol*, 2008, 86(3):105-112). In this work it has been discovered that both activated NFκB/RelA and the bromodomain protein BRD4 are major regulators of EMT. Severe asthma is characterized by resistance to steroid therapy. Severe (i.e., steroid-resistant) asthma can also be identified by molecular phenotyping as described in U.S. Pat. No. 8,053,199 to Brasier et al.

In certain aspects a subject is administered a BRD4 inhibitor or a CDK9 inhibitor.

BRD4 is a member of the BET family, which includes BRD2, BRD3, BRD4 and BRDT. The BET family are proteins that play a role in regulation of gene transcription. JQ1 is a selective BET bromodomain (BRD) inhibitor that inhibits Brd4 (Bromodomain-containing 4). Brd4 forms complexes with chromatin via two tandem bromodomains (BD1 and BD2) that bind to acetylated lysine residues in histones and Brd4 association with acetylated chromatin is believed to regulate the recruitment of elongation factor b and additional transcription factors to specific promoter regions. The nuclear protein in testis (NUT) gene is known to form fusions with Brd4 that create a potent oncogene, leading to rare, but highly lethal tumors referred to as NUT midline carcinomas (NMC). JQ1 inhibits recruitment and binding of Brd4 to TNFα and E-selectin promoter elements, and accelerates recovery time in FRAP (fluorescence recovery after photobleaching) assays using GFP-Brd4. Thus JQ1/SGCBD01 is a useful tool to study the role of Brd4 in transcriptional initiation. BRD4 inhibitors include JQ1.

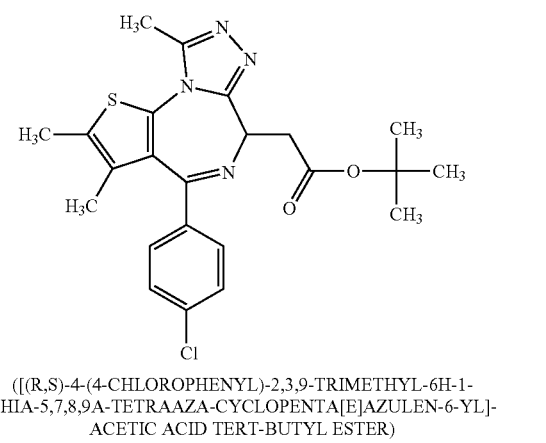

JQ1

([(R,S)-4-(4-CHLOROPHENYL)-2,3,9-TRIMETHYL-6H-1-THIA-5,7,8,9A-TETRAAZA-CYCLOPENTA[E]AZULEN-6-YL]-ACETIC ACID TERT-BUTYL ESTER)

CDK family members are highly similar to the gene products of S. cerevisiae cdc28, and S. pombe cdc2, and known as important cell cycle regulators. This kinase was found to be a component of the multiprotein complex TAK/P-TEFb, which is an elongation factor for RNA polymerase II-directed transcription and functions by phosphorylating the C-terminal domain of the largest subunit of RNA polymerase II. This protein forms a complex with and is regulated by its regulatory subunit cyclin T or cyclin K. One example of a CDK9 inhibitor is CAN508 or LDC000067.

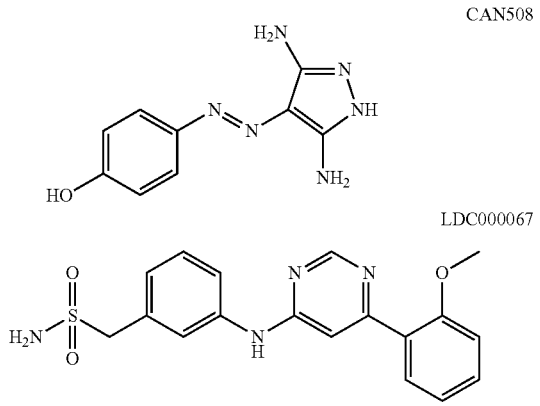

I. Anti-Inflammatory Agents

In certain aspects of the invention an anti-inflammatory agent may be used in combination with a composition described herein.

Steroidal anti-inflammatories for use herein include, but are not limited to fluticasone, beclomethasone, any pharmaceutically acceptable derivative thereof, and any combination thereof. As used herein, a pharmaceutically acceptable derivative includes any salt, ester, enol ether, enol ester, acid, base, solvate or hydrate thereof. Such derivatives may be prepared by those of skill in the art using known methods for such derivatization.

Fluticasone—Fluticasone propionate is a synthetic corticosteroid. Fluticasone propionate is a white to off-white powder and is practically insoluble in water, freely soluble in dimethyl sulfoxide and dimethylformamide, and slightly soluble in methanol and 95% ethanol. In an embodiment, the formulations of the present invention may comprise a steroidal anti-inflammatory (e.g., fluticasone propionate).

Beclomethasone—In certain aspects the steroidal anti-inflammatory can be beclomethasone dipropionate or its monohydrate. The compound may be a white powder and is very slightly soluble in water (Physicians' Desk Reference), very soluble in chloroform, and freely soluble in acetone and in alcohol.

Providing steroidal anti-inflammatories according to the present invention may enhance the compositions and methods of the invention by, for example, attenuating any unwanted inflammation. Examples of other steroidal anti-inflammatories for use herein include, but are not limited to, betamethasone, triamcinolone, dexamethasone, prednisone, mometasone, flunisolide and budesonide.

In accordance with yet another aspect of the invention, the non-steroidal anti-inflammatory agent may include aspirin, sodium salicylate, acetaminophen, phenacetin, ibuprofen, ketoprofen, indomethacin, flurbiprofen, diclofenac, naproxen, piroxicam, tebufelone, etodolac, nabumetone, tenidap, alcofenac, antipyrine, amimopyrine, dipyrone, ammopyrone, phenylbutazone, clofezone, oxyphenbutazone, prexazone, apazone, benzydamine, bucolome, cinchopen, clonixin, ditrazol, epirizole, fenoprofen, floctafeninl, flufenamic acid, glaphenine, indoprofen, meclofenamic acid, mefenamic acid, niflumic acid, salidifamides, sulindac, suprofen, tolmetin, nabumetone, tiaramide, proquazone, bufexamac, flumizole, tinoridine, timegadine, dapsone, diflunisal, benorylate, fosfosal, fenclofenac, etodolac, fentiazac, tilomisole, carprofen, fenbufen, oxaprozin, tiaprofenic acid, pirprofen, feprazone, piroxicam, sudoxicam, isoxicam, celecoxib, Vioxx®, and/or tenoxicam.

II. Formulations and Administration

The pharmaceutical compositions disclosed herein may be administered via the respiratory system of a subject. In certain aspects the compositions are deposited in the lung by methods and devices known in the art. Therapeutic compositions described herein may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations contain a preservative to prevent the growth of microorganisms. The pharmaceutical forms suitable for inhalation include sterile aqueous solutions or dispersions and sterile powders for the extemporaneous preparation of sterile inhalable solutions or dispersions. In all cases the form is typically sterile and capable of inhalation directly or through some intermediary process or device. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. The prevention of the action of microorganisms can be brought about by various antibacterial and antifungal agents, for example, parabens, chlorobutanol, phenol, sorbic acid, thimerosal, and the like.

Some variation in dosage will necessarily occur depending on the condition of the subject being treated and the particular circumstances involving exposure or potential exposure. The person responsible for administration will, in any event, determine the appropriate dose for the individual subject. Moreover, for human administration, preparations should meet sterility, pyrogenicity, general safety, and purity standards as required by FDA Office of Biologics standards or other similar organizations.

Sterile compositions are prepared by incorporating the active components in the required amount in the appropriate solvent with various other ingredients enumerated above, as required, followed by, for example, filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile compositions, some methods of preparation are vacuum-drying and freeze-drying techniques which yield a powder of the component(s) and/or active ingredient(s) plus any additional desired ingredient from a previously sterile-filtered solution.

Pulmonary/respiratory drug delivery can be implemented by different approaches, including liquid nebulizers, aerosol-based metered dose inhalers (MDI's), sprayers, dry powder dispersion devices and the like. Such methods and compositions are well known to those of skill in the art, as indicated by U.S. Pat. Nos. 6,797,258; 6,794,357; 6,737,045; and 6,488,953—all of which are incorporated by reference. According to the invention, at least one pharmaceutical composition can be delivered by any of a variety of inhalation or nasal devices known in the art for administration of a therapeutic agent by inhalation. Other devices suitable for directing pulmonary or nasal administration are also known in the art. Typically, for pulmonary administration, at least one pharmaceutical composition is delivered in a particle size effective for reaching the lower airways of the lung or sinuses. Some specific examples of commercially available inhalation devices suitable for the practice of this invention are Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), Aerotech II® or the like.

All such inhalation devices can be used for the administration of a pharmaceutical composition in an aerosol. Such aerosols may comprise either solutions (both aqueous and non-aqueous) or solid particles. Metered dose inhalers typically use a propellant gas and require actuation during inspiration. See, e.g., WO 98/35888 and WO 94/16970. Dry powder inhalers use breath-actuation of a mixed powder. See U.S. Pat. Nos. 5,458,135 and 4,668,218; PCT publications WO 97/25086, WO 94/08552 and WO 94/06498; and European application EP 0237507, each of which is incorporated herein by reference in their entirety. Nebulizers produce aerosols from solutions, while metered dose inhalers, dry powder inhalers, and the like generate small particle aerosols. Suitable formulations for administration include, but are not limited to nasal spray or nasal drops, and may include aqueous or oily solutions of a composition described herein.

A spray comprising a pharmaceutical composition described herein can be produced by forcing a suspension or solution of a composition through a nozzle under pressure. The nozzle size and configuration, the applied pressure, and the liquid feed rate can be chosen to achieve the desired output and particle size. An electrospray can be produced, for example, by an electric field in connection with a capillary or nozzle feed.

A pharmaceutical composition described herein can be administered by a nebulizer such as a jet nebulizer or an ultrasonic nebulizer. Typically, in a jet nebulizer, a compressed air source is used to create a high-velocity air jet through an orifice. As the gas expands beyond the nozzle, a low-pressure region is created, which draws a composition through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer.

In an ultrasonic nebulizer, high-frequency electrical energy is used to create vibrational, mechanical energy, typically employing a piezoelectric transducer. This energy is transmitted to the composition creating an aerosol.

In a metered dose inhaler (MDI) or in other device that us propellant, a propellant, a composition, and any excipients or other additives are contained in a canister as a mixture with a compressed gas. Actuation of the metering valve releases the mixture as an aerosol. Pharmaceutical compositions for use with a metered-dose inhaler device will generally include a finely divided powder containing a composition of the invention as a suspension in a non-aqueous medium, for example, suspended in a propellant with the aid of a surfactant. The propellant can be any conventional material employed for this purpose such as chlorofluorocarbon, a hydrochlorofluorocarbon, a hydrofluorocarbon, or a hydrocarbon including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a subject. The preparation of an aqueous composition that contains a polypeptide or peptide as an active ingredient is well understood in the art.

III. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example I

Bromodomain-4 Mediates NFκB-Dependent Epithelial Messenchymal Transition by Stabilizing the Transcriptional Elongation Complex Kinetics of TGFβ induced Type II EMT in hSAECs. A model has been established a model of TGFβ-induced type II EMT using a continuously replicating line of human small airway epithelial cells (hSAECs) (Kalita et al., *Biomed Res Int*, 2013, 505864; Ramirez et al., *Cancer Res*, 2004, 64(24): 9027-9034). To illustrate the cell state change, the distribution of F-actin was detected by confocal fluorescence microscopy after staining with Alexa568-conjugated phalloidin in control and TGFβ-stimulated hSAECs. In unstimulated cells, hSAECs assume a cuboidal morphology with perinuclear cytoplasmic distribution of F-actin (FIG. 1A, panel A). In response to chronic TGFβ stimulation, the cells acquired an elongated shape with markedly induced stress fiber formation (FIG. 1A, panel E). These morphological changes of enhanced front-rear polarity and actin rearrangement are characteristic of the type II EMT (Kalita et al., *Biomed Res Int*, 2013, 505864; Huang et. al., *J Cell Sci*, 2012, 125(19):4417-22).

Additionally, cells were subjected to immunohistochemistry by staining with primary antibodies to the mesenchymal markers SNAI1 and vimentin (VIM), or antibody to the epithelial marker CDH1, and imaged via confocal fluorescence microscopy to examine these proteins' expression and intracellular distribution. In unstimulated hSAECs, SNAI1 is detected in a punctate nuclear pattern, with no detectable cytoplasmic signal. After induction of the EMT, SNAI1 is distributed more broadly throughout the nucleus in larger aggregates, and appears in the cytoplasm (FIG. 1A, panels B, F). By contrast, CDH1 staining is intense and diffusely cytoplasmic in unstimulated hSAECs, and disappears after induction of the EMT (FIG. 1A, panels C, G). Faint cytoplasmic VIM expression is detected in unstimulated hSAECs heterogeneously distributed in a perinuclear pattern; in the EMT state VIM becomes much more intense and ordered, consistent with its organization into cytosolic intermediate filaments (FIG. 1A, panels D, H). These results show that chronic TGFβ stimulation increases core EMT transcription factor and mesenchymal marker expression while decreasing CDH1 expression, suggesting full activation of the EMT program.

Figure 1B:
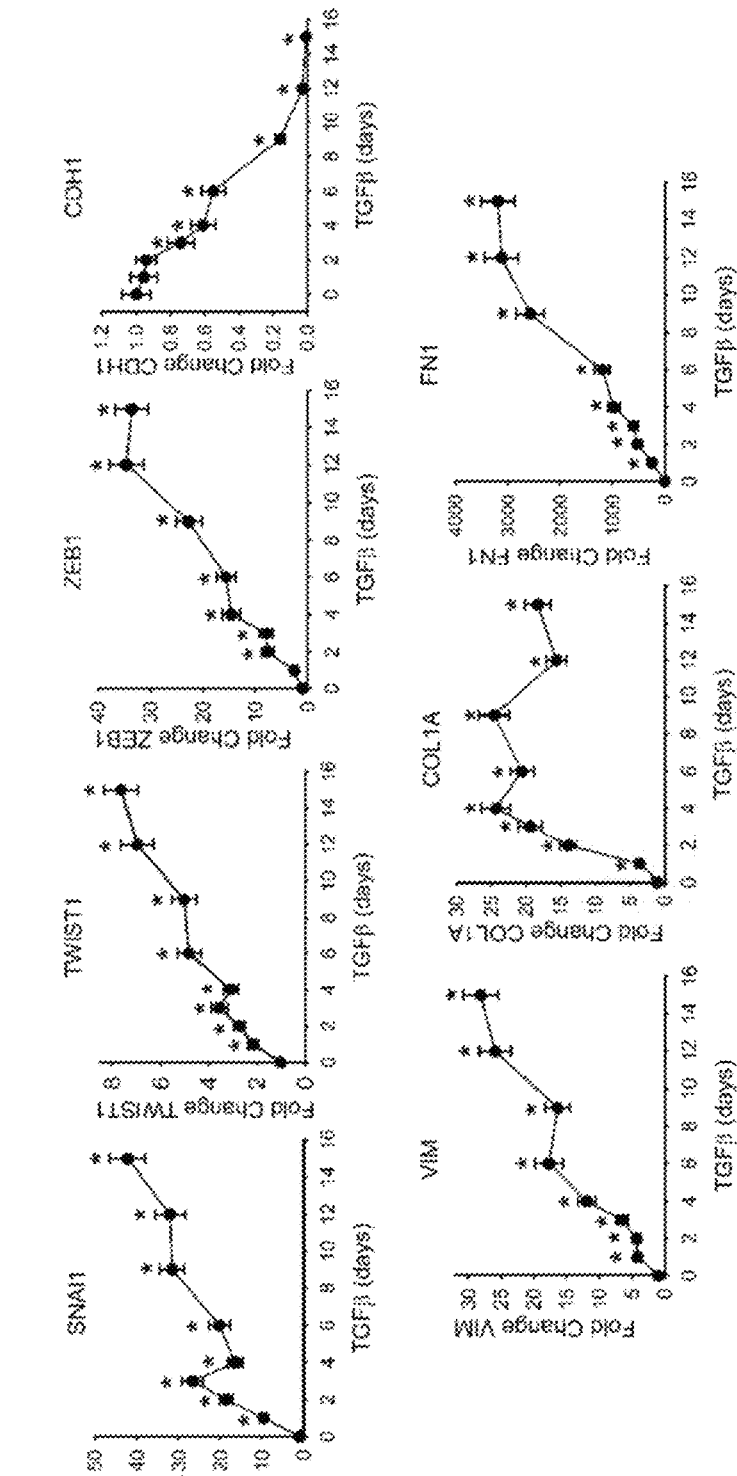

To quantify the dynamic changes in expression of mesenchymal genes and EMT-associated transcription factors during induction of type II EMT, hSAECs stimulated with TGFβ were sampled in a time-course experiment for up to 15 d; the core EMT transcriptional regulators, mesenchymal genes and epithelial genes were measured by Q-RT-PCR. The inventors observed a consistent biphasic expression of SNAI1, first detectable at 10-fold within the first day of TGFβ treatment, followed by a brief spike at 3 d, then subsequently increasing to ~42-fold by 15 d, consistent with its complex post-transcriptional mode of regulation by miR34 (FIG. 1B). A similar pattern was observed for TWIST1, where TGFβ induced TWIST1 2-fold by 1 d after TGFβ stimulation, peaking at 7.6-fold at 15 d. ZEB1 followed a similar pattern, but appeared to saturate at 34-fold induction 15 d after TGFβ stimulation. By contrast, expression of the epithelial marker CDH1 was stable for the first 3 days, then began falling to <0.01-fold at 15 d (FIG. 1B). The mesenchymal genes VIM and FN1 showed similar patterns of induction as that of the EMT transcription factors, with FN1 being the most robustly induced at 3,186-fold relative to day 0. The expression of COL1A peaks rapidly and apparently saturates, after peaking at 24-fold induction after 4 d of TGFβ stimulation (FIG. 1B). Together these data suggest that TGFβ induces morphological and gene signatures of Type II EMT in hSAECs (FIGS. 1A and 1B).

Figure 2A:
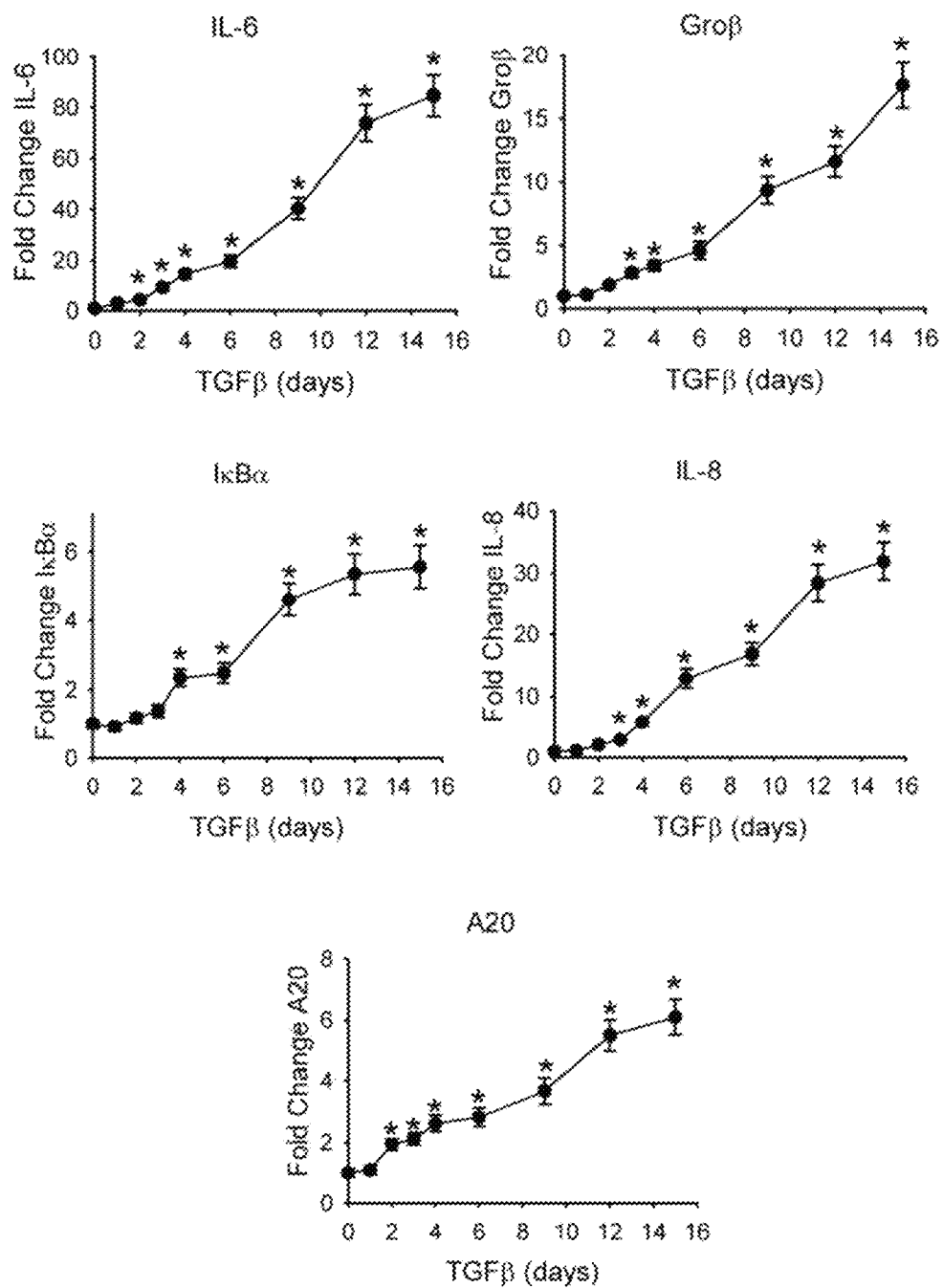
FIG. 2A-2C. Activation of the NFκB signaling pathway in TGFβ-treated hSAECs. (A) TGFβ induces NF-κB-dependent gene expression in hSAECs. hSAECs were incubated with a time series of TGFβ (10 ng/mL) up to 15 days. The expression of the NFκB-dependent genes IL-6, Groβ, IκBα, IL-8, and A20 was examined by Q-RT-PCR. Shown is the fold-change in mRNA abundance normalized to cyclophilin. (B) TGFβ induces RelA abundance. Whole-cell extracts of hSAECs were isolated and IPed with primary anti-RelA Ab. RelA abundance was quantified by SID-SRM-MS, normalized to the input protein concentration. (C) TGFβ induces RelA nuclear translocation. hSAECs were incubated with a time series of TGFβ (10 ng/mL) up to 15 d. 150 µg of nuclear extracts were processed for Western blot using anti-RelA Ab (upper panel). Lamin B was detected as a loading control (lower panel). Lower panel: Quantification of nuclear RelA from Odyssey infrared imager. ANOVA was performed looking for time differences, followed by Tukey's post hoc test to determine significance. *=$p<0.05$ compared to without TGFβ. Data are the means±S.D. from n=3 independent experiments.

Chronic TGFβ treatment activates the NFκB signaling pathway. Earlier studies using unbiased RNA-seq demonstrated that TGFβ induced a subnetwork of NFκB-dependent genes (Tian et al., 2015, BMC. Genomics. 16:529). Because the NFκB-dependent network is under phospho-specific control (Brasier et al., 2011, J Virol. 85:11752-69; Nowak et al., 2008, Mol. Cell. Biol. 28:3623-38) a panel of phospho-Ser276 RelA-dependent immediate-early stress genes (IL-6, CXCL2/Groβ and IL8) were measured, and those regulated by the phospho-Ser276 RelA-independent pathway (NFKBIA/IκBα and TNFAIP3/A20) (Brasier et al., 2011, J. Virol. 85:11752-69; Nowak et al., 2008, Mol. Cell. Biol. 28:3623-38). It was observed that TGFβ treatment robustly induced the expression of IL-6 in a manner similar to that of the core EMT transcription factors, with the mesenchymal genes being weakly induced by 2 d and peaking at 85-fold after 15 d (FIG. 2A). The expression patterns of CXCL2/Groβ, NFKBIA/IκBα, IL-8, and TNFAIP3/A20 were superimposable. Finally, it was noted that the IL6, CXCL2/Groβ, and IL-8 genes, all induced by phospho-Ser276 RelA, were the most highly upregulated, peaking at ~85, ~18, and 32-fold, respectively, after 15 d of stimulation, vs those of NFKBIA/IκBα and TNFAIP3/A20, which were both induced by ~6-fold (FIG. 2A). These data suggest that TGFβ preferentially triggers the phospho-Ser276 RelA NFκB gene network during induction of the EMT.

Figure 2B:
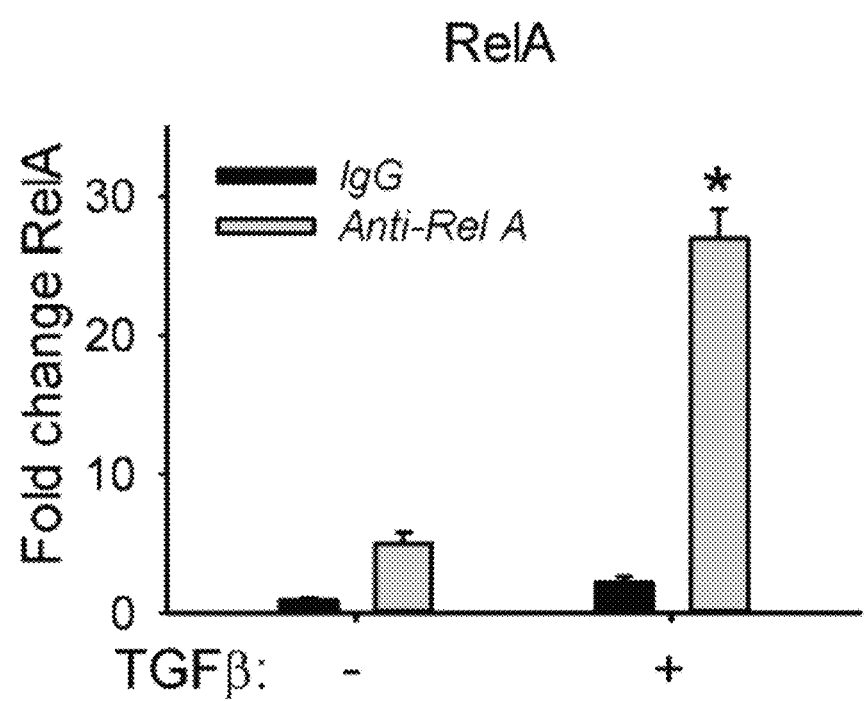

The TGFβ program activates nuclear NFκB/RelA. To examine the mechanism for TGFβ-induced transcriptional reprogramming of the NFκB gene program, the total cellular RelA abundance was measured using a quantitative immunoprecipitation (IP)-selected reaction monitoring assay (SID-SRM-MS) (Zhao et al., 2013, Mol. Cell. Proteomics. 12:1513-29; Zhao, et al., 2011, Mol. Cell. Proteomics. 10:M111). In this assay, whole-cell extracts of control or EMT hSAECs were isolated, IPed (immunoprecipitated) with control IgG or anti-RelA Ab, and the immune complexes analyzed by SID-SRM-MS, normalized by the input protein concentration. In each cell state the RelA signal was significantly enriched in the anti-RelA IP compared to that with IgG, indicating selective enrichment of RelA (FIG. 2B). Comparison of the RelA abundance in the anti-RelA IPs showed that RelA was 5-fold enriched in the EMT vs unstimulated hSAECs (FIG. 2B).

Figure 2C:
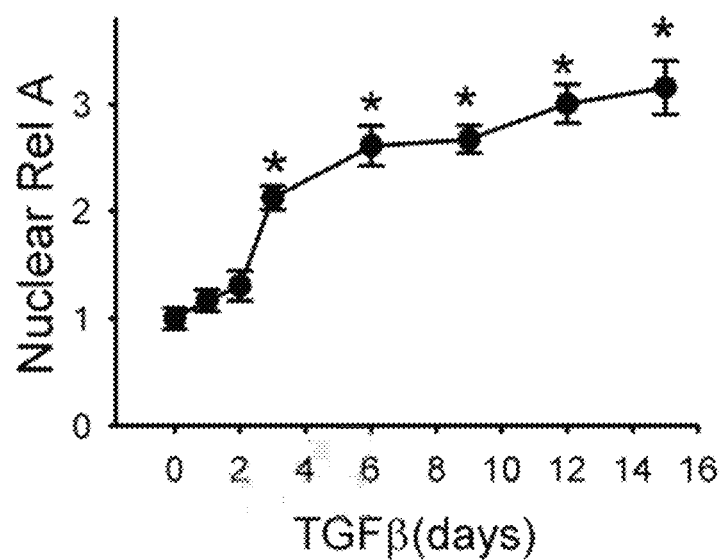

Next the relative abundance of nuclear RelA was measured. hSAECs were enriched by sucrose cushion centrifugation and the abundance of RelA determined by Western blot; it has been shown that these nuclear preparations are free of cytoplasmic contamination (Tian et al., 2015, BMC. Genomics. 16:529; Brasier et al., 2011, J. Virol. 85:11752-69; Nowak et al., 2008, Mol. Cell. Biol. 28:3623-38). It was observed that nuclear RelA levels were significantly increased in comparison with that of mock treatment, first detectable after 3 d of TGFβ stimulation, with a 3.2-fold induction 15 d after TGFβ addition (FIG. 2C). Together these data indicate that TGFβ induces RelA expression and enhances nuclear translocation.

Figure 3A:
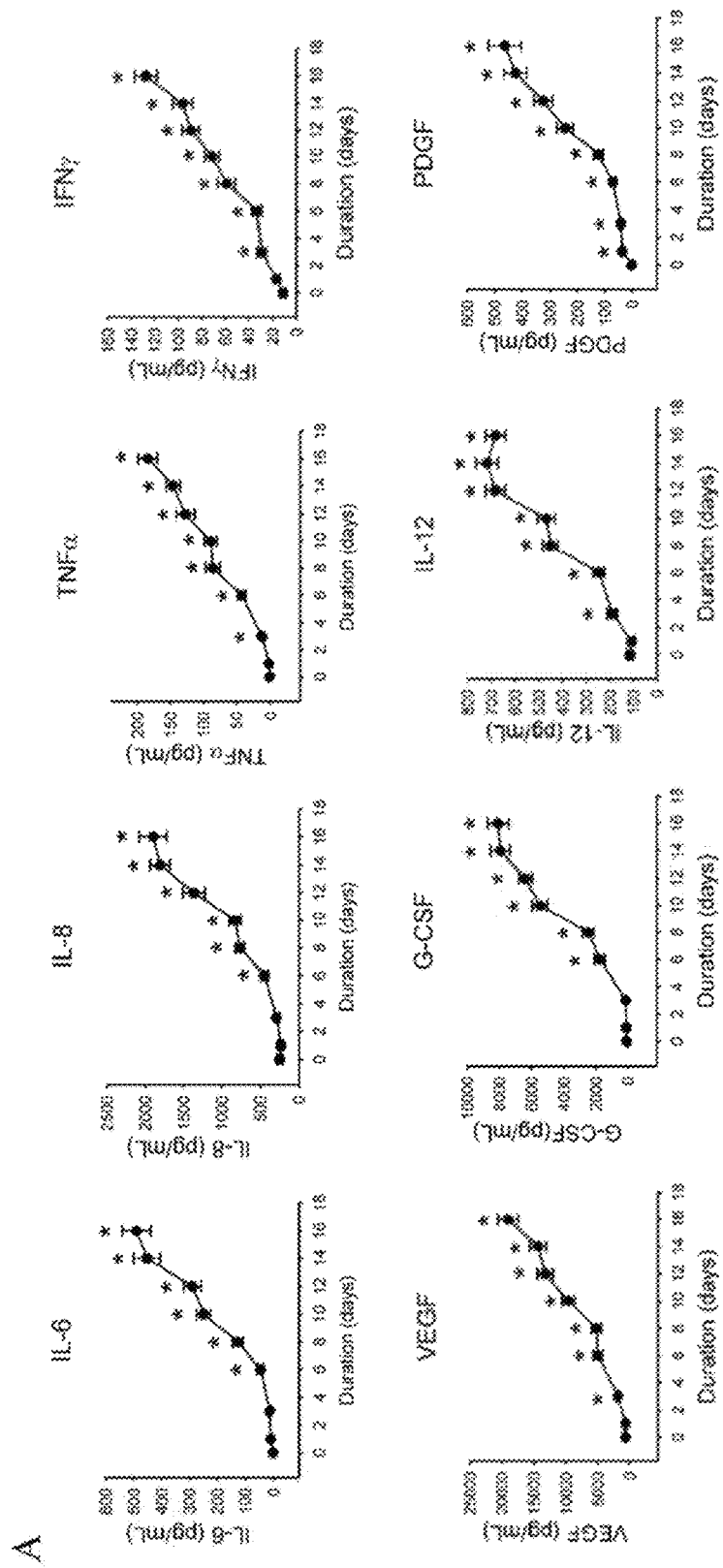
FIG. 3A-3B. Activation of the NFκB signaling pathway in TGFβ-treated hSAECs. (A) TGFβ induces secretion of NF-κB-dependent cytokines/chemokines. hSAECs were incubated with a time series of TGFβ (10 ng/mL) up to 16 d. The conditioned medium was collected for cytokine determination by multiplex ELISA. Shown are the changes in IL-6, IL-8, TNFα, IFNγ, VEGF, G-CSF, IL-12, and PDGF levels. (B) Conditioned medium from TGFβ-treated cells induces RelA nuclear translocation in naive hSAECs. Naive hSAECs were incubated for 1h with conditioned mediums from TGFβ-treated hSAECs. Left panel: 150 µg of nuclear extracts were processed for Western blot using anti-RelA Ab, with Lamin B as the loading control. Right panel: Quantification of nuclear RelA from Odyssey infrared imager. All data shown are the mean ±S.D. from n=3 experiments. ANOVA was performed looking for time differences, followed by Tukey's post hoc test to determine significance. *=$p<0.05$ compared with control epithelial cells.
Figure 3B:
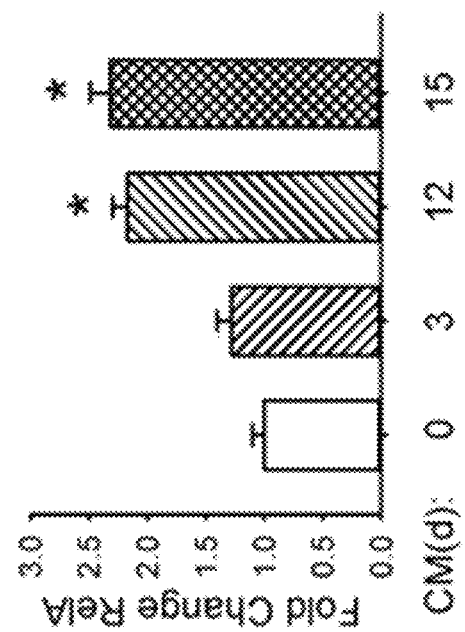
Figure 3B:
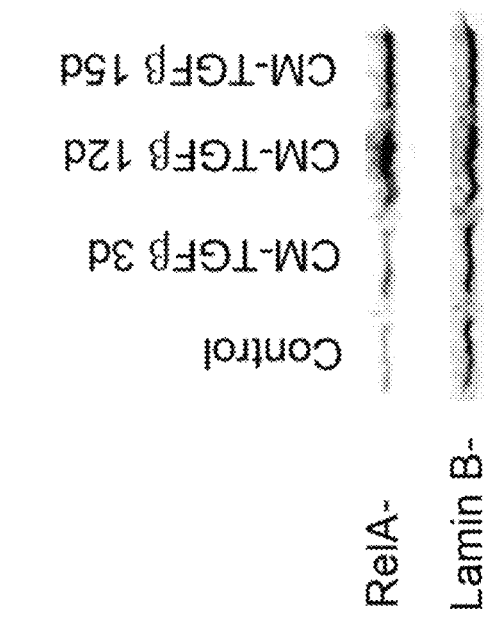

To explore the mechanism of TGFβ-induced NFκB, conditioned medium from a time course of TGFβ-stimulated hSAECs was collected and cytokine secretion measured by multiplex ELISA. It was observed that TGFβ induced secretion of IL-6, IL-8, TNFα, IFNγ, VEGF, G-CSF, IL-12, and PDGF—all NFκB-dependent cytokine/chemokines (FIG. 3A). To examine whether NFκB activation was direct or paracrine, conditioned medium (CM) from hSAECs treated with TGFβ for 3, 12 or 15 d was added to naïve hSAECs. One hour later, nuclei were fractionated and the abundance of nuclear RelA was measured by Western blot. It was observed that nuclear RelA levels were 2.3-fold higher in hSAECs stimulated with 15 d CM vs controls (FIG. 3B). Interpreted with our earlier RNA-Seq study (Tian et al., 2015, BMC. Genomics. 16:529), the inventors conclude that TGFβ induces a paracrine factor important for TGFβ-induced NFκB activation (Korkaya et al., 2012, Mol. Cell. 47:570-84).

TGFβ induces epigenetic reprogramming of NFκB-dependent immediate-early genes. In systems modeling studies of the EMT, it was observed that TGFβ promoted more efficient coupling of the NFκB canonical and cross-talk pathways (Kalita et al., 2013, Biomed. Res. Int. 2013: 505864). To determine whether the NFκB signaling response was functionally altered by the EMT, normal or EMT-hSAECs were challenged with a battery of prototypical innate activators, including TNFα, a ligand that activates NFκB via TNFRI (Tian et al., 2005, J. Biol. Chem. 280: 17435-48); Sendai (SeV), Respiratory Syncytial- and candid 1, RNA viruses that activate NFκB via the RIG-I-MAVS pathway (Brasier et al., 2011, J. Virol. 85:11752-69; Liu et al., 2007, J. Virol. 81:1401-11; Huang et al., 2012, PLoS. Negl. Trop. Dis. 6:e1659); poly(I:C), a pathogen-associated molecular pattern (PAMP) that activates NFκB via Toll-like receptor (TLR)-3 (Alexopoulou et al., 2001, Nature. 413: 732-38); and lipopolysaccharide (LPS), a PAMP that activates NFκB via TLR4 (Fitzgerald et al., 2003, J. Exp. Med.

Figure 4A:
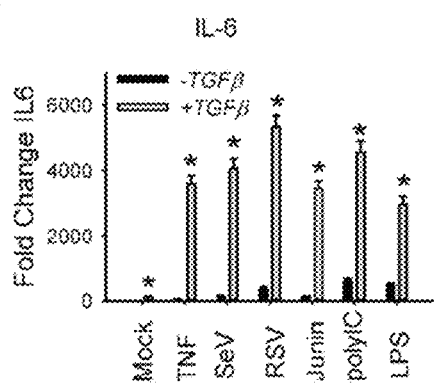
FIG. 4A-4B. Requirement of NF-κB signaling for the TGFβ-induced Type II EMT. (A) Efficiency of shRNA RelA depletion. hSAECs stably expressing RelA shRNA were cultured for 5 days with/without 2 µg/ml doxycycline and the protein levels of RelA in whole-cell lysates of cells were examined by Western blots (left panel). Afterwards, cells were treated with 25 ng/ml TNFα for 0 or 1 hour and the cells harvested. Total cellular RNA was extracted and the expression of IL-6 and IκBα mRNAs measured by Q-RT-PCR. Data are the means±S.D. from n=3 experiments. *=$p<0.05$ compared with mock treatment. (B) RelA depletion blocks TGFβ-induced EMT gene expression. hSAECs stably expressing RelA shRNA were cultured for 5 days with/without 2 µg/ml doxycycline for inducible RelA depletion. Afterwards, cells were treated with 10 ng/ml TGFβ for 0 or 15 d and the cells harvested. The RNA samples were examined for the expression of RelA, IL-6, SNAI1 ZEB1, TWIST1, VIM, and FN1. Tukey's post hoc test was performed to determine significance. *=$p<0.05$ compared to control siRNA.
Figure 4A:
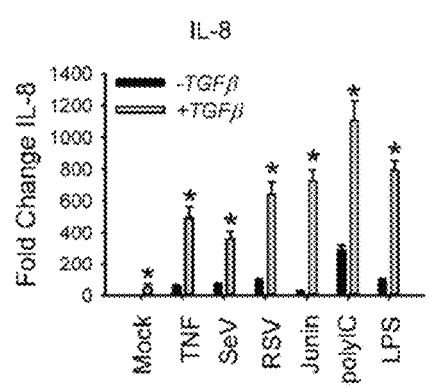

198:1043-55). It was observed that TNF induced IL-6 expression 50-fold in hSAECs, but by 3,600-fold in EMT-hSAECs (FIG. 4A). This extraordinarily high level of NFκB-dependent gene induction was observed across all activators, and for other members of the immediate-early gene network (FIG. 4A).

Figure 4B:
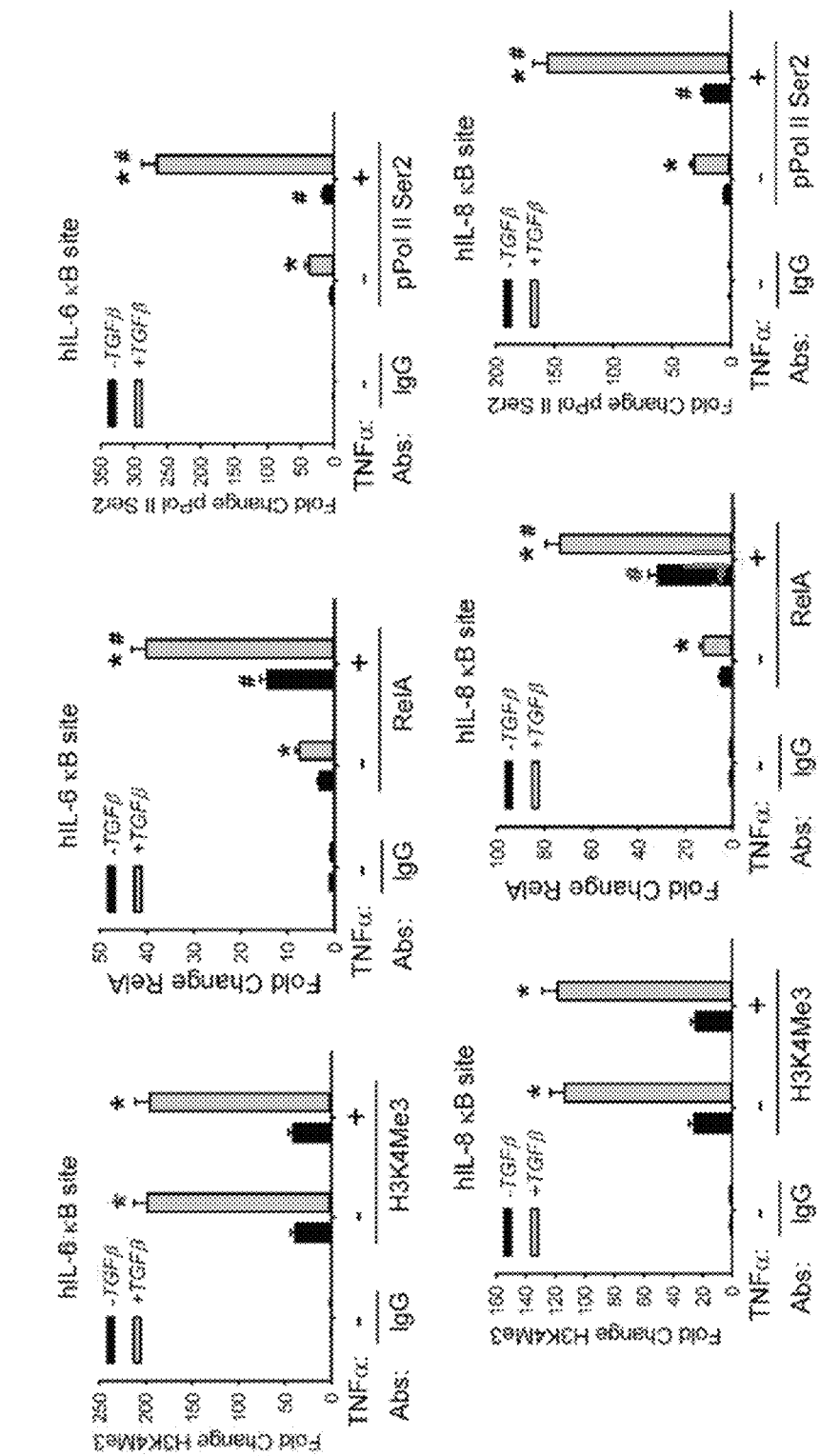

Previous studies indicated that TGF-β-mediated EMT is associated with epigenetic modifications at specific genetic loci, including induction of the euchromatin mark H3-Lys (K)4 trimethyl (Me3)(Kalita et al., 2013, *Biomed. Res. Int.* 2013:505864; McDonald et al., 2011, *Nat. Struct. Mol. Biol.* 18:867-74). To examine whether TGFβ induces epigenetic reprogramming of the immediate-early genes as a mechanism for their functional hyperinducibility, the inventors quantitated H3K4Me3 binding using a highly quantitative two-step chromatin immunoprecipitation (XChIP) assay (Nowak et al., 2005, *Biotechniques.* 39:715-25; Tian et al., 2012, *Methods. Mol. Biol.* 809:105-20) (FIG. 4B). It was found that H3K3Me3 binds to the 5' NFκB site in the IL-6 promoter, and was induced 5-fold by TGFβ (FIG. 4B, primers are shown in Table II). The inventors similarly examined the binding of RelA and the hallmark of transcriptional elongation, phospho-Ser 2 RNA Pol II. Enhanced RelA binding was observed in EMT hSAECs over that in control hSAECs. More strikingly, an 18-fold increase in TNFα-induced phospho-Ser2 CTD RNA Pol II binding was observed compared to that in control hSAECs (FIG. 4B). Similar observations were also found in the IL-8 promoter (FIG. 4B). The evidence above indicates that TGFβ-induced type II EMT-related epigenetic reprogramming of NFκB gene loci could be responsible for their hyperinduction in the mesenchymal state.

TABLE 1

PCR primers for q-RT-PCR

| Primer Set | Sequence (5'-3') Forward | Sequence (5'-3') Reverse |
|---|---|---|
| hRelA | CCGGACCGCTGCATCCACAG (SEQ ID NO: 1) | AGTCCCCACGCTGCTCTTCT (SEQ ID NO: 2) |
| hBRD4 | ACCTCCAACCCTAACAAGCC (SEQ ID NO: 3) | TTTCCATAGTGTCTTGAGCACC (SEQ ID NO: 4) |
| hFN1 | CGGTGGCTGTCAGTCAAAG (SEQ ID NO: 5) | AAACCTCGGCTTCCTCCATAA (SEQ ID NO: 6) |
| hCOL1A | CCAGAAGAACTGGTACATCAGCA (SEQ ID NO: 7) | CGCCATACTCGAACTGGAATC (SEQ ID NO: 8) |
| hIL-6 | CTGGATTCAATGAGGAGACTTGC (SEQ ID NO: 9) | TCAAATCTGTTCTGGAGGTACTCTAGG (SEQ ID NO: 10) |
| hSNAI1 | GCGCTCTTTCCTCGTCAGG (SEQ ID NO: 11) | GGGCTGCTGGAAGGTAAACTCT (SEQ ID NO: 12) |
| hTWIST1 | TCTCGGTCTGGAGGATGGA (SEQ ID NO: 13) | CAATGACATCTAGGTCTCCG (SEQ ID NO: 14) |
| hVIM | GCTCAATGTTAAGATGGCCCTT (SEQ ID NO: 15) | TGGAAGAGGCAGAGAAATCCTG (SEQ ID NO: 16) |
| hZEB1 | GATGATGAATGCGAGTCAGATGC (SEQ ID NO: 17) | GATGATGAATGCGAGTCAGATGC (SEQ ID NO:18) |
| hIL-8 | AAGACATACTCCAAACCTTTCCACC (SEQ ID NO: 19) | CAATAATTTCTGTGTTGGCGCA (SEQ ID NO: 20) |
| hGrorβ | CACACTCAAGAATGGGCAGA (SEQ ID NO: 21) | GCTTCCTCCTTCCTTCTGGT (SEQ ID NO: 22) |
| hTNFAIP3 | TCCTCAGGCTTTGTATTTGAGC (SEQ ID NO: 23) | TGTGTATCGGTGCATGGTTTTA (SEQ ID NO: 24) |
| hNFKBIA | CTCCGAGACTTTCGAGGAAATAC (SEQ ID NO: 25) | GCCATTGTAGTTGGTAGCCTTCA (SEQ ID NO: 26) |
| hCDH1 | CGAGAGCTACACGTTCACGG (SEQ ID NO: 27) | GGGTGTCGAGGGAAAAATAGG (SEQ ID NO: 28) |
| hPPIA | CCCACCGTGTTCTTCGACATT (SEQ ID NO: 29) | GGACCCGTATGCTTTAGGATGA (SEQ ID NO: 30) |
| mIL-6 | TAGTCCTTCCTACCCCAATTTCC (SEQ ID NO: 31) | TTGGTCCTTAGCCACTCCTTC (SEQ ID NO: 32) |
| mSNAI1 | CACACGCTGCCTTGTGTCT (SEQ ID NO: 33) | GGTCAGCAAAAGCACGGTT (SEQ ID NO: 34) |
| rnZEB1 | ACCGCCGTCATTTATCCTGAG (SEQ ID NO: 35) | CATCTGGTGTTCCGTTTTCATCA (SEQ ID NO: 36) |
| mTWIST1 | GGACAAGCTGAGCAAGATTCA (SEQ ID NO: 37) | CGGAGAAGGCGTAGCTGAG (SEQ ID NO: 38) |
| mCOL1A1 | GCTCCTCTTAGGGGCCACT (SEQ ID NO: 39) | CCACGTCTCACCATTGGGG (SEQ ID NO: 40) |
| mVIM | CGTCCACACGCACCTACAG (SEQ ID NO: 41) | GGGGGATGAGGAATAGAGGCT (SEQ ID NO: 42) |
| mαSMA | GTCCCAGACATCAGGGAGTAA (SEQ ID NO: 43) | TCGGATACTTCAGCGTCAGGA (SEQ ID NO: 44) |

TABLE 1-continued

PCR primers for q-RT-PCR

| Primer Set | Sequence (5'-3') Forward | Sequence (5'-3') Reverse |
|---|---|---|
| mFN1 | ATGTGGACCCCTCCTGATAGT (SEQ ID NO: 45) | GCCCAGTGATTTCAGCAAAGG (SEQ ID NO: 46) |
| mPPIA | GAGCTGTTTGCAGACAAAGTTC (SEQ ID NO: 47) | CCCTGGCACATGAATCCTGG (SEQ ID NO: 48) |

TABLE 2

Primer sets for XChip

| Gene | Sequence (5'→3') Forward | Reverse |
|---|---|---|
| hSNAI1-5'κB | ACGTCAGCTGAAGGGAAACAAACA (SEQ ID NO: 49) | CGGTTCAGGCAGCTGCACTCTT (SEQ ID NO: 50) |
| hZEB1-5'κB | TGGTTCCCCTGAACTTTACTGT (SEQ ID NO: 51) | TGGGCACCAGAGGCATGATA (SEQ ID NO: 52) |
| hVIM-5'κB | CCAGGCATCTGCCACAATG (SEQ ID NO: 53) | CACTCAAGAGCTTCCCAGCAA (SEQ ID NO: 54) |
| hIL-6-5'κB | TCGTGGGGAAATGTGTCCAG (SEQ ID NO: 55) | CTGGCCGAGTTCCAGCAG (SEQ ID NO: 56) |

Figure 5A:
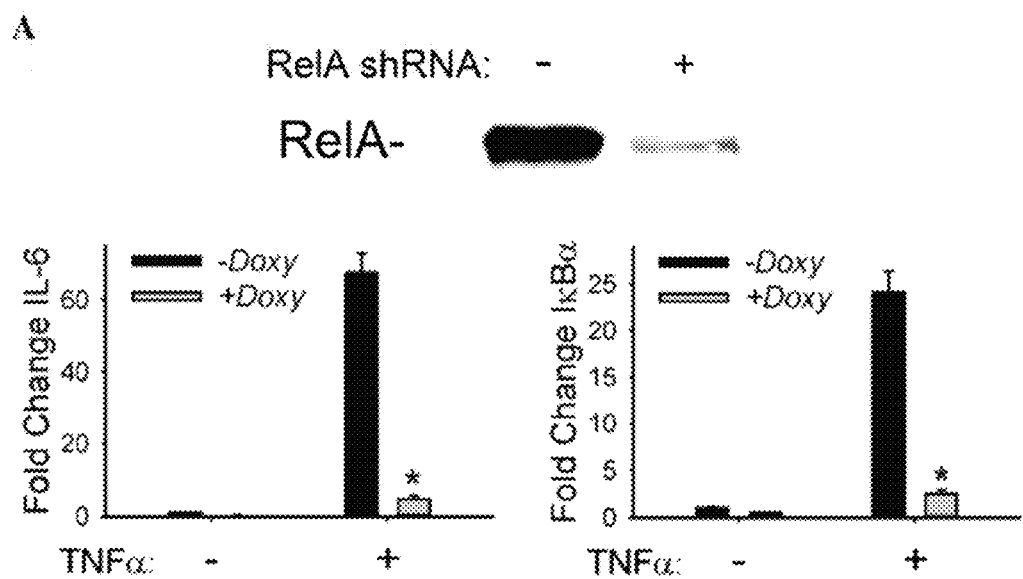
FIG. 5A-5B. TGFβ induces a paracrine factor important for TGFβ-induced NFκB activation. (A) Efficiency of shRNA RelA depletion. hSAECs stably expressing RelA shRNA were cultured for 5 days with/without 2 µg/ml doxycycline and the protein levels of RelA in whole-cell lysates of cells were examined by Western blots (left panel). Afterwards, cells were treated with 25 ng/ml TNFα for 0 or 1 hour and the cells harvested. Total cellular RNA was extracted and the expression of IL-6 and IκBα mRNAs measured by Q-RT-PCR. Data are the means±S.D. from n=3 experiments. *=$p<0.05$ compared with mock treatment. (B) RelA depletion blocks TGFβ-induced EMT gene expression. hSAECs stably expressing RelA shRNA were cultured for 5 days with/without 2 µg/ml doxycycline for inducible RelA depletion. Afterwards, cells were treated with 10 ng/ml TGFβ for 0 or 15 d and the cells harvested. The RNA samples were examined for the expression of RelA, IL-6, SNAI1, ZEB1, TWIST1, VIM, and FN1. Tukey's post hoc test was performed to determine significance. *=$p<0.05$ compared to control siRNA.

Requirement for NFκB/RelA in the type II EMT program. It was previously observed a requirement for IKK in the TGFβ-induced EMT in hSAECs using a small-molecule inhibitor. To extend these studies, the inventors examined the effect of NFκB/RelA-mediated silencing using doxycycline (Dox)-inducible shRNA. hSAECs stably expressing control or RelA-directed shRNA were cultured for 5 d±Dox (2 μg/ml) to induce shRNA expression. RelA abundance in WCEs was quantified by Western immunoblots, and showed a dramatic 90% decrease in RelA protein abundance in the stable RelA-shRNA-expressing hSAECs (FIG. 5A, left panel). In these cells, the robust TNFα-inducible expression of IL6 and IκBα mRNA was almost completely blocked in the stable RelA-shRNA-expressing hSAECs (FIG. 5A, right panel). Together these data indicate that RelA shRNA functionally inhibits RelA signaling.

Figure 5B:
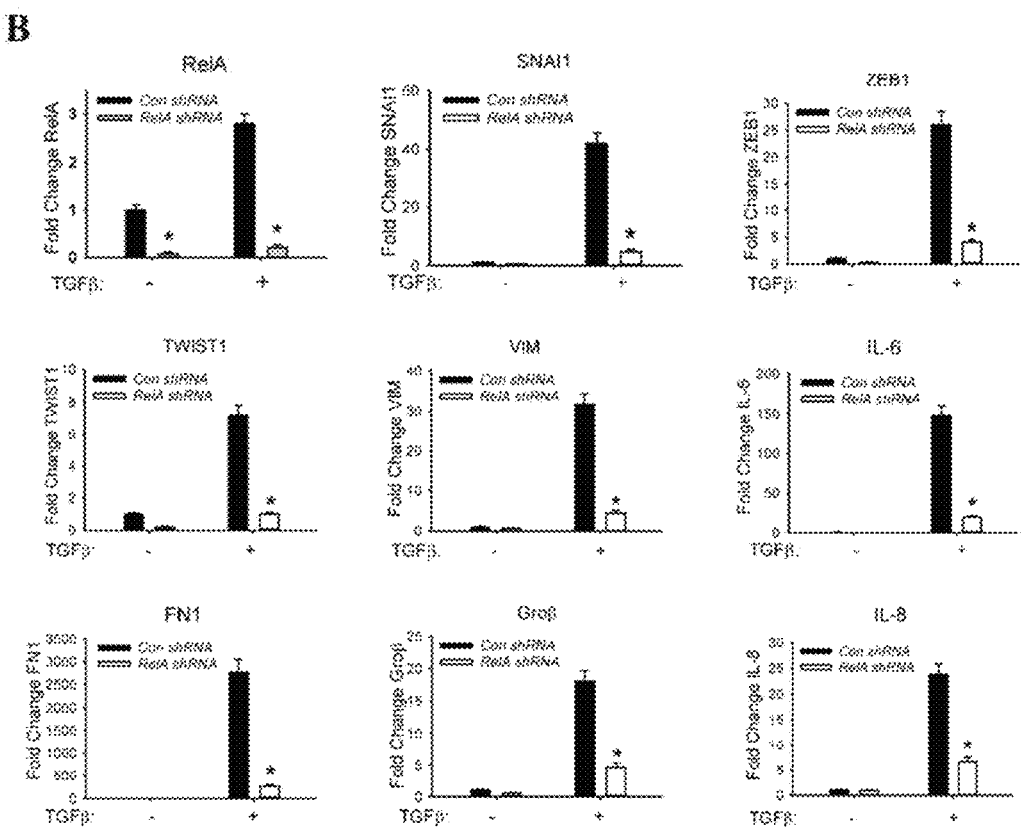
Figure 6A:
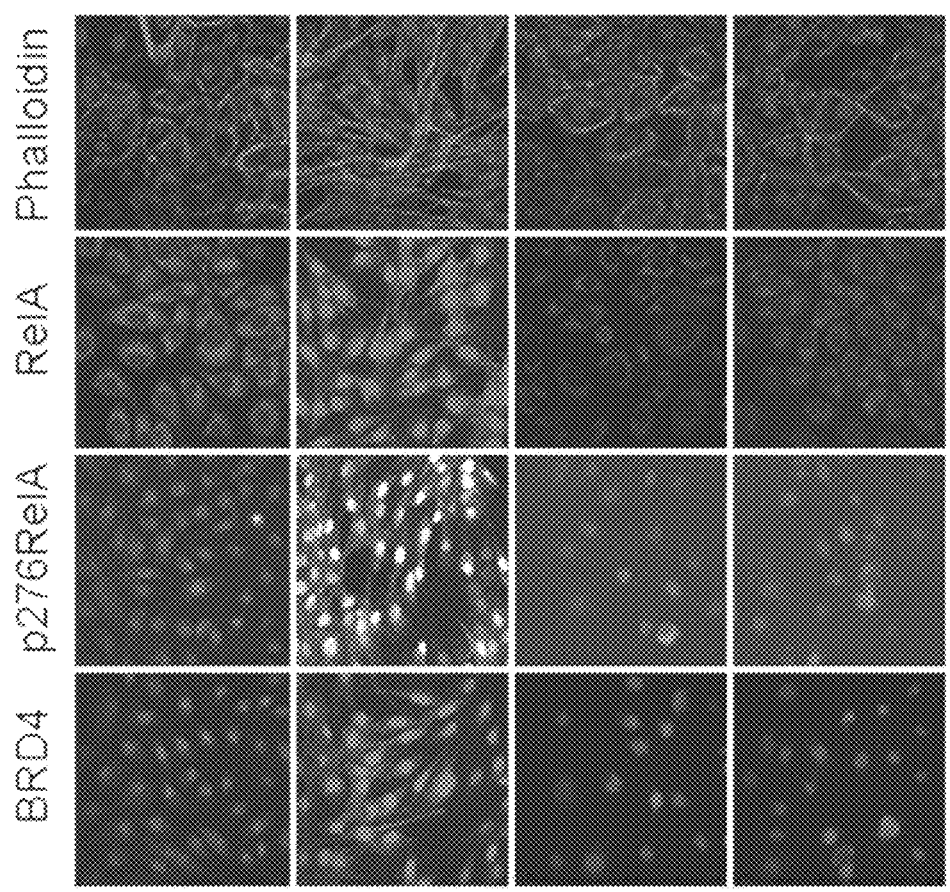
FIG. 6A-6B. Requirement of RelA Ser276 phosphorylation for the TGFβ-induced Type II EMT. (A) Immunocytochemical studies of RelA, BRD4, and phospho-Ser276 RelA. Both RelA+/+ and RelA−/− hSAECs were incubated in the absence or presence of TGFβ (10 ng/mL) for 15 d. Cells were fixed, stained with Alexa568-conjugated phalloidin and DAPI, and examined by confocal microscopy. Separate coverslips were subjected to immunofluorescence by incubation with primary RelA, BRD4, or phospho-Ser276 RelA Abs, then stained with Alexa Fluor 488, 568, and 647-conjugated Goat anti-rabbit IgGs, respectively, counterstained with DAPI, and imaged via fluorescence microscopy to examine these proteins' levels and intracellular distribution. (B) Quantification of phospho-Ser 276 RelA and total RelA in whole-cell extracts using quantitative IP-SID-SRM-MS. Both RelA+/+ and RelA−/− hSAECs were incubated in the absence or presence of TGFβ (10 ng/mL) for 15 d and WCEs were obtained. Equal amounts of WCE were IPed with pan anti-RelA Ab and subjected for SID-SRM-MS analysis using a phospho-Ser276 RelA prototypic peptide. Shown are changes in relative abundance relative to control cells. *=$p<0.05$ compared to without TGFβ.

To determine the role of NFκB/RelA in the TGFβ-induced EMT, hSAECs stably expressing control or RelA-directed shRNA were induced with Dox and subsequently were or were not stimulated with TGFβ (10 ng/mL) for 15 d. RelA shRNA silencing significantly inhibited TGFβ-induced enhanced SNAI1 expression, from 42-fold to ~6-fold, that of ZEB1 from 25-fold to ~3.5-fold, and of TWIST1 from 8.5-fold to ~1.5-fold (FIG. 5B), indicating that RelA is required for TGFβ-induced EMT gene expression. Furthermore, the results of the immuno-cytochemical studies showed that RelA shRNA silencing significantly inhibited TGFβ-induced morphological changes characteristic of type II EMT; RelA nuclear translocation; and the cellular distribution of BRD4 in hSAECs (FIG. 6A).

Figure 6B:
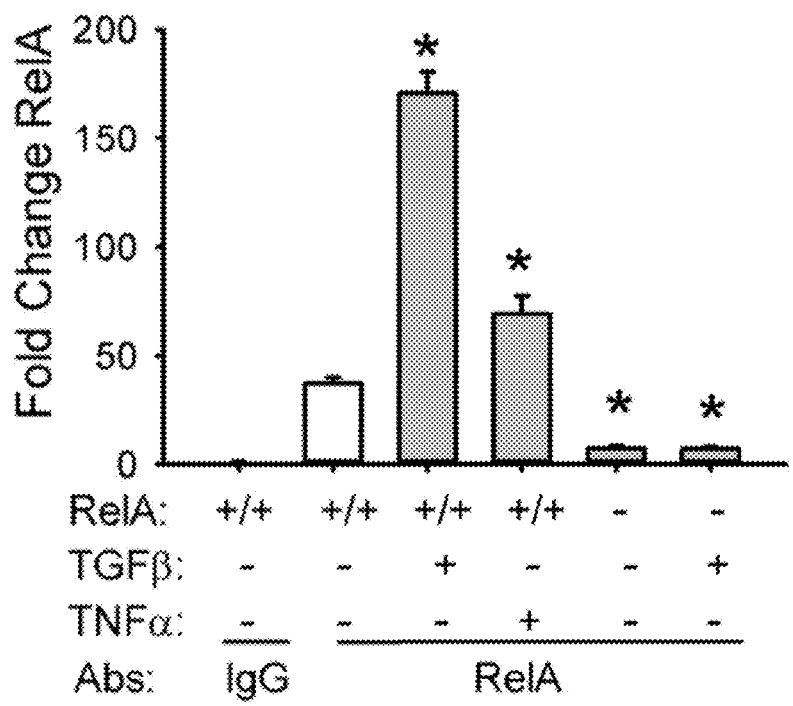
Figure 6B:
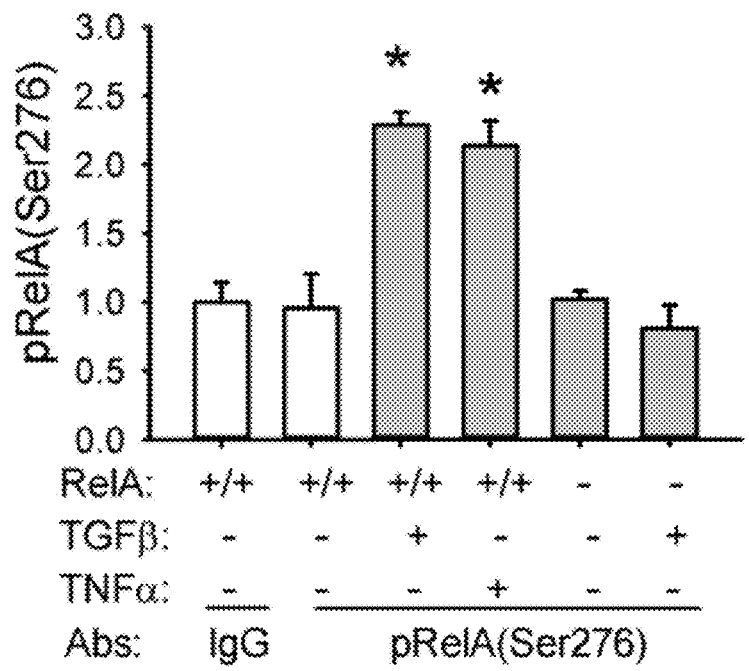

NF-κB/RelA Ser276 phosphorylation is required for activation of the type II EMT program. Based on the inventors' findings that TGFβ preferentially activates phospho-Ser276-dependent immediate-early genes (FIG. 2A), the inventors next examined whether NFκB RelA Ser276 phosphorylation is required for the TGFβ-induced EMT. For this purpose, immuno-cytochemical staining of phosphor Ser 276 RelA was performed and it was found that chronic TGFβ treatment significantly elevated the level of RelA Ser 276 phosphorylation (FIG. 6A). Meanwhile, RelA shRNA silencing significantly inhibited TGFβ-induced RelA Ser 276 phosphorylation, along with the morphological changes characteristic of the type II EMT in hSAECs (FIG. 6A). In addition, the abundance of phospho-Ser 276 RelA along with total RelA was quantitated in WCEs using a quantitative IP-SID-SRM-MS assay (FIG. 6B). Equal amounts of WCE were immunoprecipitated with pan anti-RelA Ab and subjected to SID-SRM-MS analysis using a phospho-Ser276 RelA prototypic peptide. TNFα, a potent monokine inducer of RelA Ser 276 phosphorylation, was used as a positive control. It was found that both chronic TGFβ treatment and acute TNF treatment significantly enriched the levels of phospho-Ser 276 RelA in hSAECs (FIG. 6B). As a measure of specificity, the phospho-Ser 276 RelA signal was abolished in RelA shRNA-depleted cells (FIG. 6B), as was the total RelA signal (FIG. 6B).

Finally, as an independent confirmation, previously characterized RelA$^{-/-}$ mouse embryonic fibroblasts (MEFs) that were stably transfected with either FLAG-EGFP-tagged wild-type RelA (RelA WT) or an FLAG-EGFP-tagged non-phosphorylatable Ser276-to-Ala mutation (RelA Ser276Ala) were examined. The time course of mSNAI1, mTwist1, mZEB1, and mIL-6 gene expression in response to TGFβ was examined in both cell types by Q-RT-PCR. It was found that TGFβ induced mSNAI1 to a lesser degree in fibroblasts than was seen in hSAECs, peaking at 4-fold; nevertheless both the basal and TGFβ-inducible mSNAI1 expression was significantly inhibited in the RelA Ser276Ala-expressing MEFs. Similarly, the 3.5-fold induction of mTwist1, the 2.8-fold induction of mZEB1, and 2.8-fold induction of mIL-6 mRNA expression in TGFβ-treated RelA WT-expressing MEFs were completely abolished in the RelA Ser276Ala-expressing MEFs. All of these data strongly suggest that RelA Ser 276 phosphorylation is required for the TGFβ-induced EMT.

NFκB/RelA is required for recruitment of the CDK9-BRD4 complex to core EMT transcription factor genes. The experimental data suggested that TGFβ-induced type II EMT is absolutely NF-κB/RelA-dependent, and implicate phospho-Ser 276 RelA. Building on previous work showing that phospho-Ser 276 RelA activates transcriptional elongation of immediate-early genes in innate signaling by recruitment of the BRD4-CDK9 complex to inducible promoters (Brasier et al., 2011, *J. Virol.* 85:11752-69; Nowak et al., 2008, *Mol. Cell. Biol.* 28:3623-38), the inventors sought to test whether this mechanism was used in the TGFβ-induced type II EMT.

TGFβ-induced transcriptional elongation complex assembly in native chromatin in the absence or presence of NFκB/RelA was examined (FIG. 7). In these experiments, XChIP assays were used with region-specific primers (Table 2) to quantify protein binding to the proximal promoters of the core EMT genes. Control or RelA-directed shRNA-expressing hSAECs were induced with Dox and stimulated with TGFβ for 0 or 15 d. The chromatin was analyzed for NFκB/RelA, CDK9, BRD4, and phospho-Ser 2 CTD RNA Pol II binding by XChIP. It was found that in control shRNA-expressing hSAECs RelA bound to the SNAI1 promoter and was further induced 4-fold by TGFβ (FIG. 7A), confirming the activation of NFκB signaling by paracrine TGFβ stimulation. In the RelA shRNA-expressing hSAECs, both the unstimulated and TGFβ-induced RelA binding was completely inhibited, confirming the effect of RelA depletion (FIG. 7A). The inventors observed that TGFβ stimulation induced a 4-fold increase in both CDK9 and BRD4 binding to the SNAI1 promoter; this induction was significantly attenuated by RelA depletion (FIG. 7A). The TGFβ induction of phospho-Ser2 CTD RNA Pol II was also blocked by RelA depletion (FIG. 7A). These data suggest that TGFβ induces direct RelA binding to the SNAI1 promoter and facilitates formation of the transcriptional elongation complex in native chromatin.

Figure 7A:
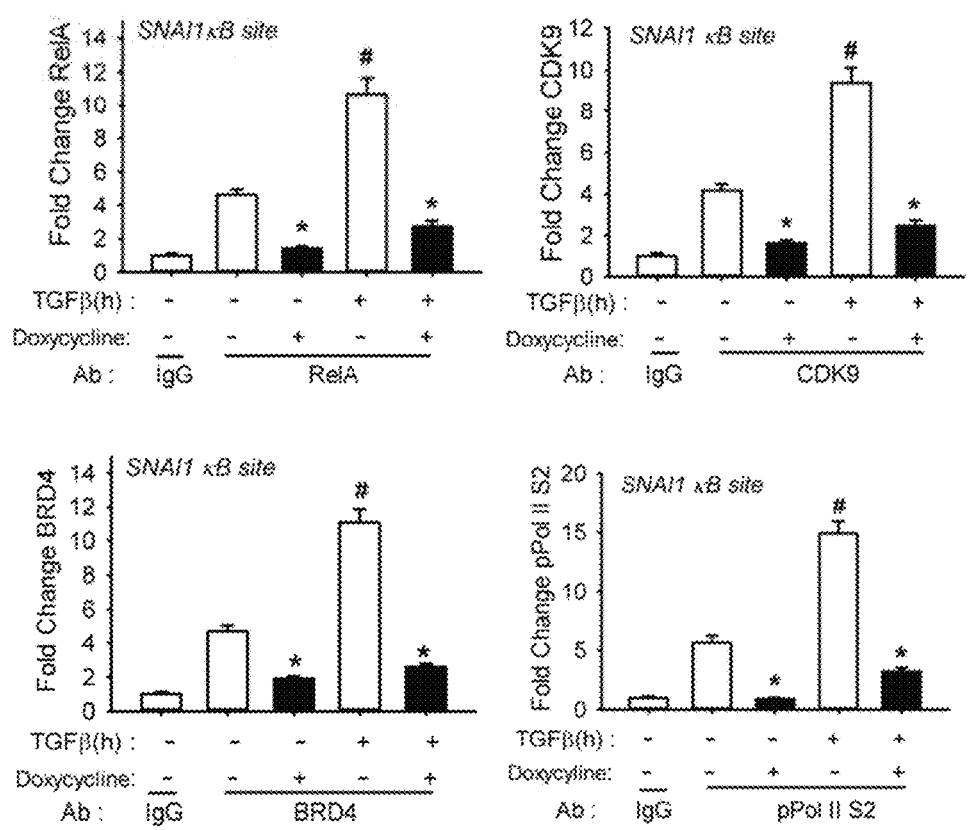
FIG. 7A-7D. NF-κB binding is required for TGFβ-induced recruitment of the CDK9/BRD4 complex to EMT genes. hSAECs stably expressing RelA shRNA were cultured for 5 ds±2 µg/ml doxycycline for inducible RelA depletion. Cells were then stimulated with TGFβ for 0 or 15 d±doxycycline, chromatin cross-linked, and subjected to IP with Abs specific for RelA, CDK9, BRD4, or RNA polymerase II CTD Ser 2 phosphorylated form (phospho-Ser2 CTD Pol II). Anti-rabbit IgG was used as the negative control. The recruitment of RelA, CDK9, BRD4, and pSer2 CTD RNA Pol II to the 5' NFκB site of the SNAI1 (A), ZEB1 (B), IL-6 (C), and VIM (D) promoters was determined by Q-gPCR. Tukey's post hoc test was performed to determine significance, *=p<0.05 compared to without doxycycline and #=p<0.05 compared to mock treatment. Data are from three independent experiments.
Figure 7B:
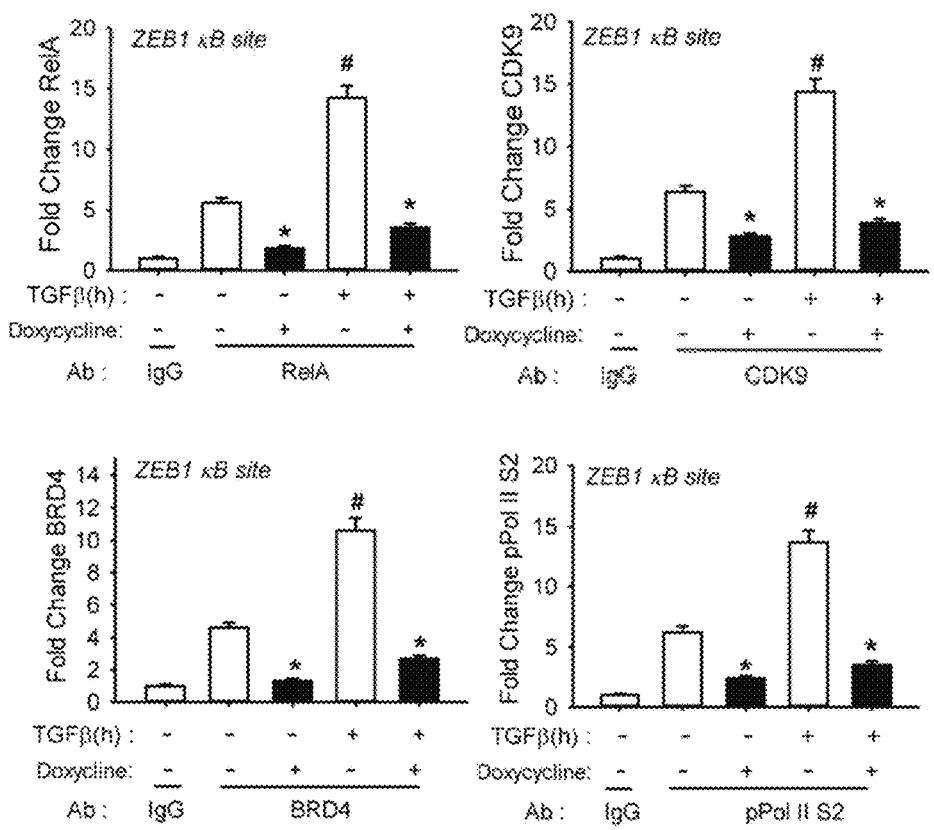
Figure 7C:
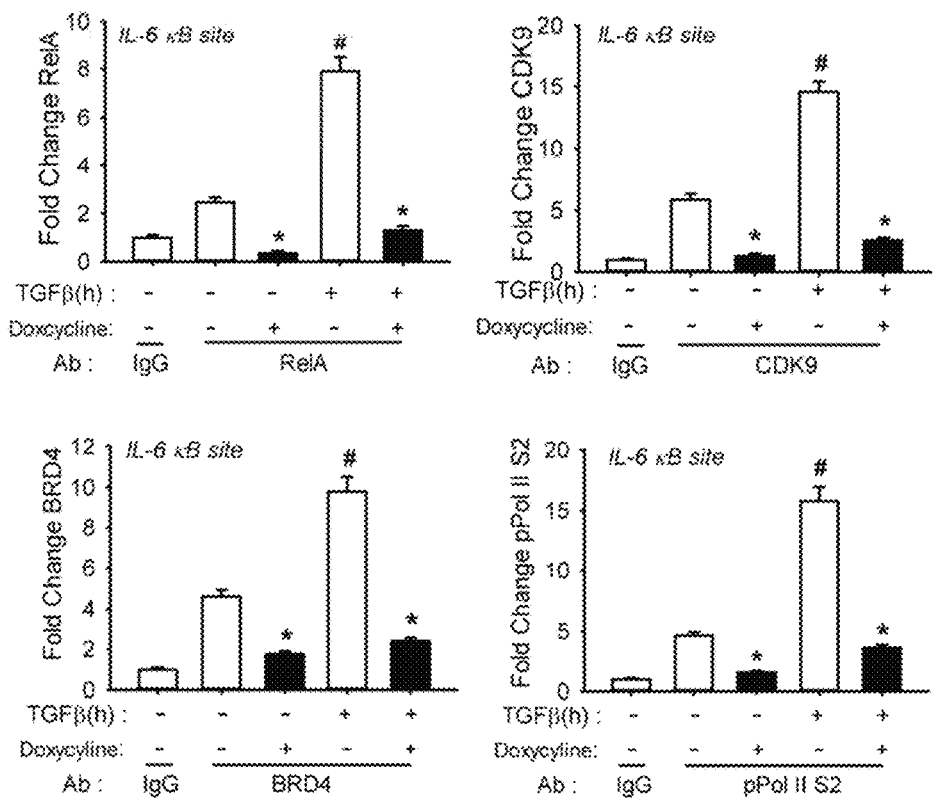
Figure 7D:
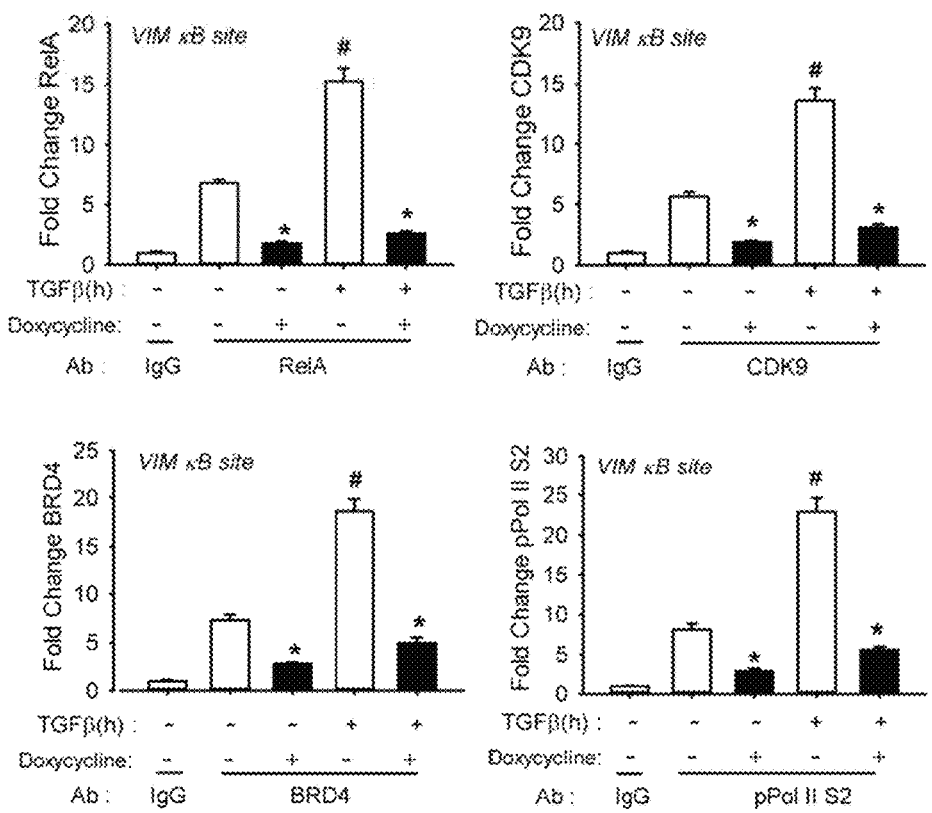

The inventors extended these findings to examine the effects of the TGFβ-induced NFκB pathway on CDK9, BRD4, and phospho-Ser$^2$ CTD RNA Pol II recruitment to the ZEB1, IL-6, and VIM promoters. Similar patterns of TGFβ-mediated induction were observed. RelA depletion inhibited RelA, CDK9, BRD4, and phospho-Ser 2 CTD RNA Pol II recruitment to all genes in a manner similar to that of SNAIL1 (FIG. 7B, 7C, and 7D).

Similar experiments were conducted in the absence or presence of the selective IκB kinase inhibitor BMS-345541 (Burke et al., 2003, *J. Biol. Chem.* 278:1450-56). BMS treatment inhibited RelA, CDK9, BRD4, and phospho-Ser 2 CTD RNA Pol II recruitment in a manner consistent with that seen in the RelA depletion experiments (FIG. 12A, 12B, 12C, and 12D). Together these results suggest that TGFβ induces NFκB/RelA-mediated recruitment of the transcriptional elongation complexes and formation of phospho-Ser 2 CTD RNA Pol II to promote the type II EMT.

Figures 8A, 8B:
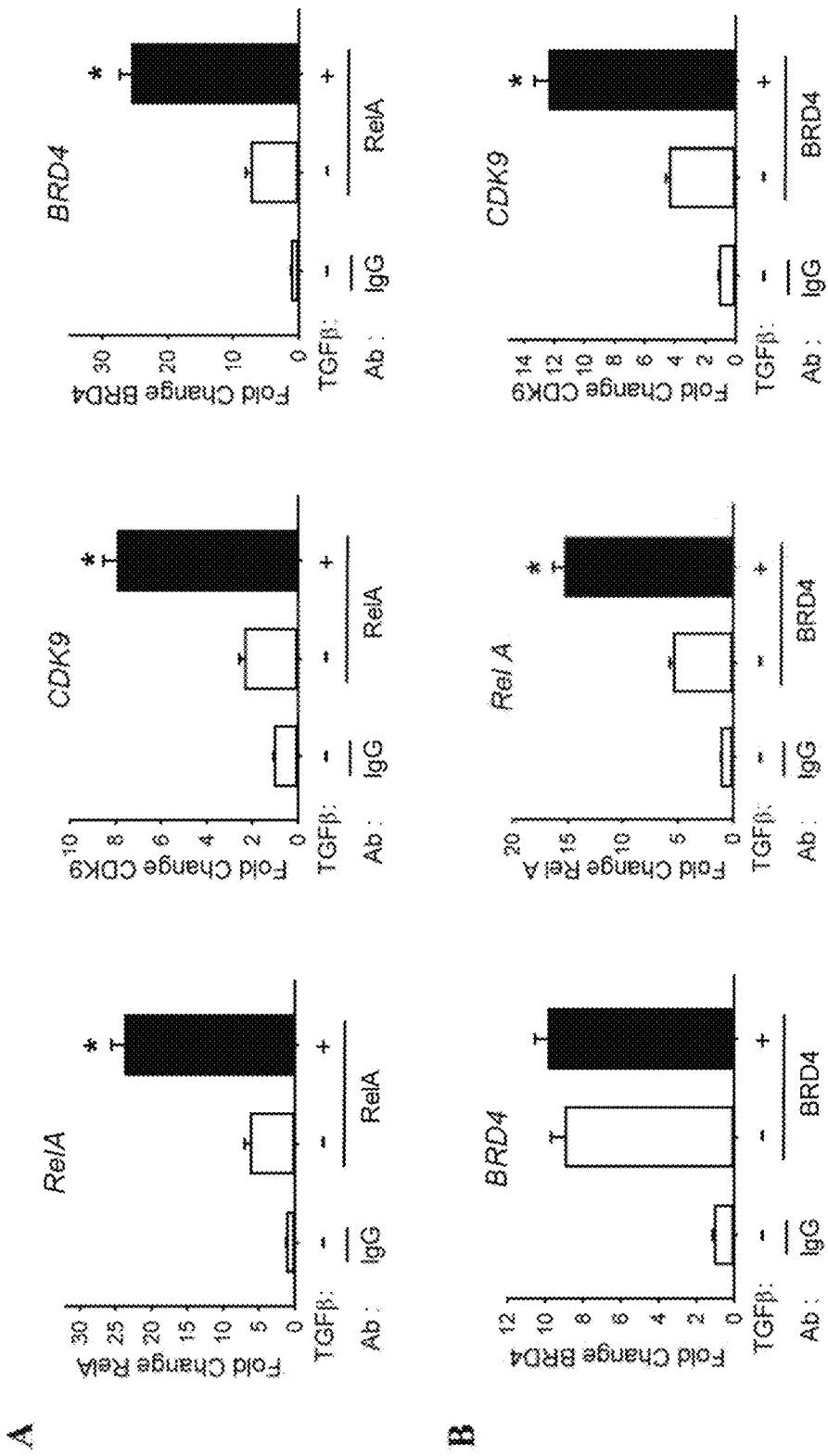
FIG. 8A-8B. TGFβ induces RelA/BRD4/CDK9 nuclear complex formation. The nuclear extracts of hSAECs with or without TGFβ stimulation were first enriched by IP with Abs to RelA or BRD4 and the IPed products analyzed for the presence of RelA, CDK9, and BRD4 proteins by SID-SRM-MS. The data are normalized by the input protein concentration and plotted as fold change over control. Controls represent samples IPed with IgG. (A) SID-SRM-MS analysis of nuclear RelA complexes. RelA, CDK9, and BRD4 protein levels were determined in the samples IPed with anti-RelA and control IgG. *=p<0.05 compared to regular hSAECs IPed with anti-RelA. (B) SID-SRM-MS analysis of nuclear BRD4 complexes. BRD4, RelA, and CDK9 protein levels were determined in the samples IPed with anti-BRD4 or control IgG. Tukey's post hoc test was performed to determine significance, *=p<0.05 compared to regular hSAECs IPed with anti-BRD4. The data are the means±S.D. from n=3 experiments.

EMT induces formation of the nuclear complex of RelA with BRD4·CDK9. BRD4 is a mammalian bromodomain protein that is a critical mediator of transcriptional elongation, functioning both to recruit activated CDK9 to the promoter and to activate it by phosphorylation (Jang et al., 2005, *Mol. Cell.* 19:523-34; Filippakopoulos et al., 2010, *Nature.* 468:1067-73). Previous work has shown that BRD4 recruitment to target genes occurs via one of two known mechanisms: (1) by binding acetylated histone H4 (H4-KAc); and (2) by association with site-specific transcription factors (Brasier et al., 2011, *J. Virol.* 85:11752-69; Jang et al., 2005, *Mol. Cell.* 19:523-34). To examine whether TGFβ stimulated formation of an active RelA.BRD4.CDK9 complex, the inventors adapted the IP-SID-SRM-MS assay for quantification of RelA-associated BRD4, and vice-versa. Nuclear extracts of control- or TGFβ-stimulated hSAECs were prepared. RelA and BRD4 complexes were separately enriched by IP with anti-RelA or anti-BRD4 Abs and the immune complexes quantified for RelA, CDK9 and BRD4 by SID-SRM-MS, normalized to the input protein concentration. Relative to the IgG control, anti-RelA Ab increased abundance of RelA; this effect was further increased upon TGFβ stimulation, consistent with RelA upregulation (FIG. 2B, 6B, and 8A, left panel). In the RelA IPs, both CDK9 and BRD4 signals were enriched by TGFβ stimulation (FIG. 8A, middle and right panels).

Although there were similar levels of BRD4 in both control and TGF-treated cells compared to that of IgG control (FIG. 8B, left panel), RelA was significantly enriched in the BRD4 immune complexes from TGFβ stimulated hSAECs (FIG. 8B, middle panel). The inventors also observed that CDK9 was significantly enriched in the BRD4 complexes (FIG. 8B, right panel), indicating that TGFβ treatment induces formation of an active RelA·BRD4·CDK9 complex.

BRD4 is required for the Type II EMT Based on its TGFβ-induced complex formation with RelA, and RelA-dependent recruitment to core EMT transcription factor genes, it is hypothesized that BRD4 recruitment is a major determinant of NFκB-dependent type II EMT initiation and transcriptional reprogramming.

Figure 9A:
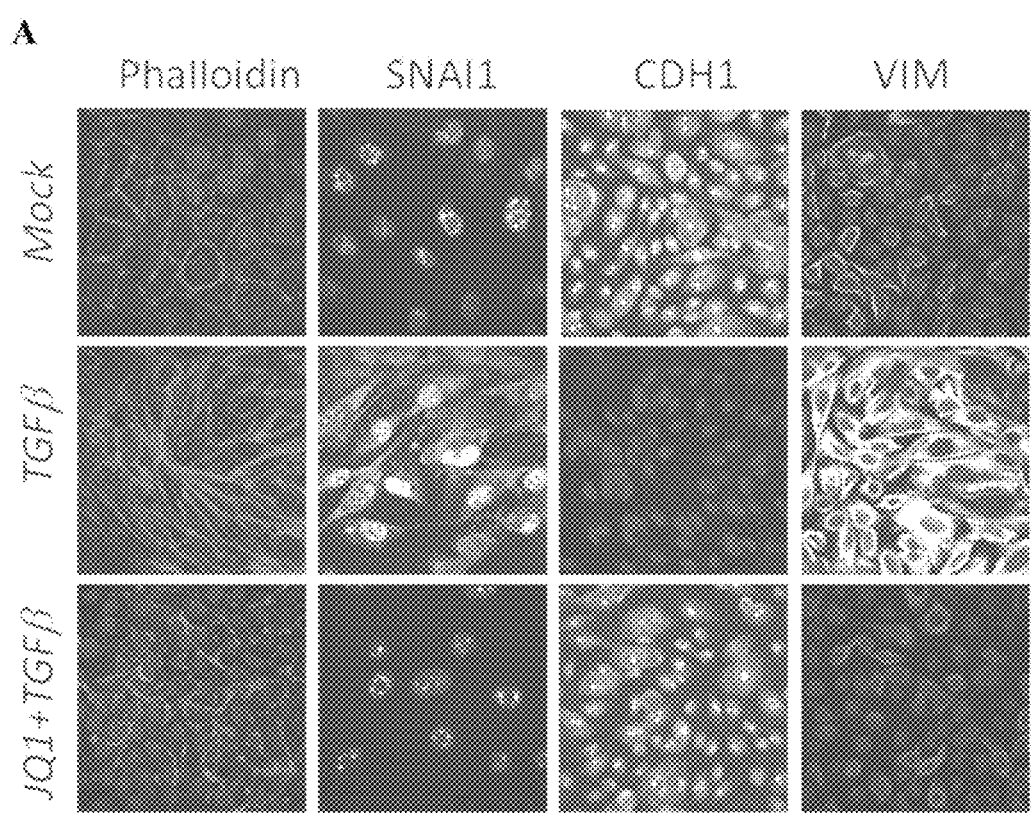
FIG. 9A-9B. Requirement of BRD4 for the Type II EMT. (A) The BRD4 inhibitor JQ1 blocks the EMT. hSAECs were pre-treated with the BRD4 inhibitor JQ1 (10 μM) ±TGFβ (10 ng/mL) for 15 days. Cells were fixed, stained with Alexa568-conjugated phalloidin and separately primary Abs for SNAI1, VIM, and CDH1, as described in FIG. 1. (B) JQ1 blocks TGFβ-induced EMT gene expression in hSAECs. hSAECs were pre-treated with JQ1 (10 μM) ±TGFβ (10 ng/mL) for 15 d. The expression of SNAI1 CDH1, VIM, ZEB1, FN1 and IL-6 mRNA was measured by Q-RT-PCR. ANOVA was performed looking for time differences, followed by Tukey's post hoc test to determine significance. *=p<0.05 compared to TGFβ only. The data are the means±S.D. from n=3 experiments.
Figure 9B:
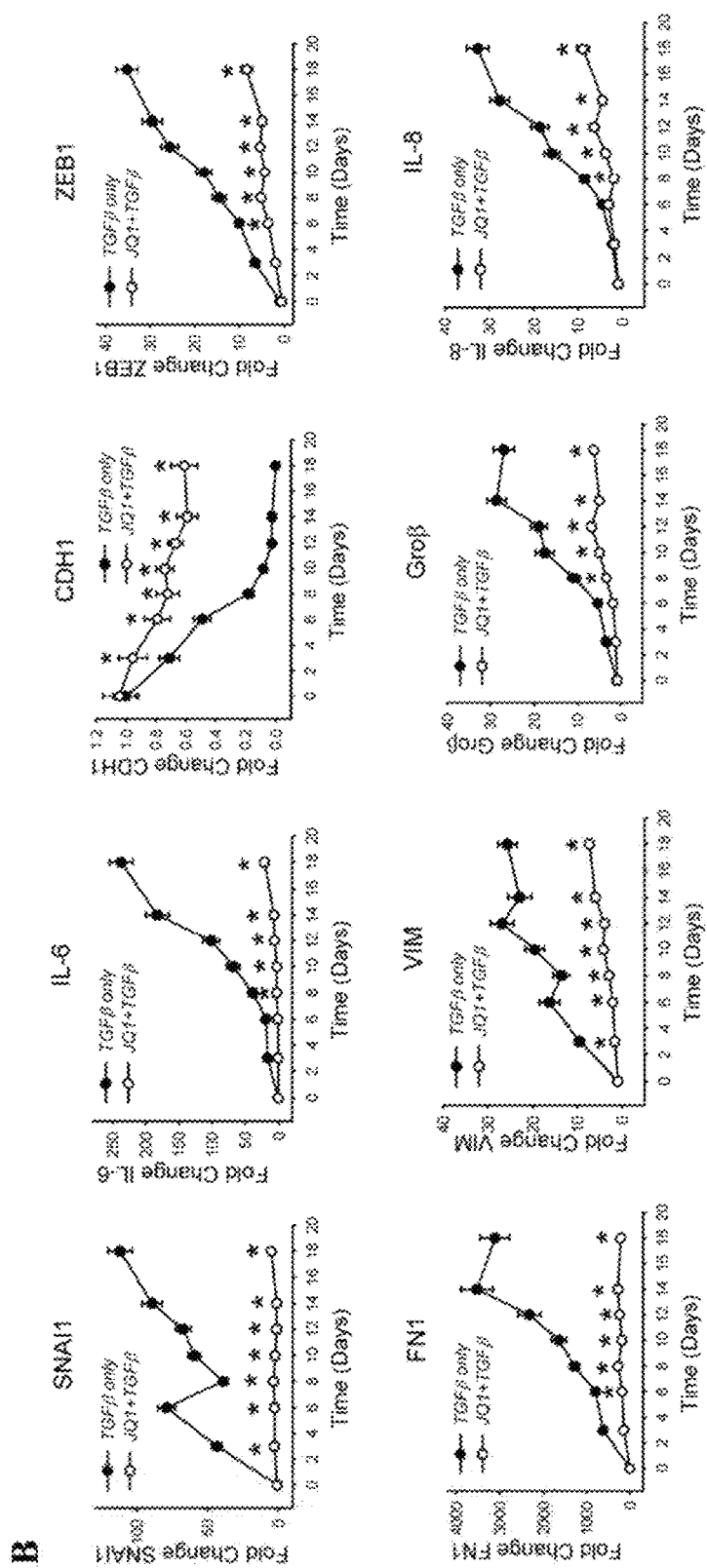

The inventors first examined the effect of the small-molecule BRD4 inhibitor JQ1 on TGFβ-induced EMT. JQ1 binds the acetyl lysine recognition pocket, displacing it from chromatin-associated acetylated histones (Filippakopoulos et al., 2010, *Nature.* 468:1067-73), providing a powerful tool to probe the role of BRD4 under physiological conditions. hSAECs were treated with solvent or JQ1 (10 μM) and TGFβ-stimulated (15 d). In vehicle-treated cells a response to TGFβ stimulation was observed; it induced hSAECs to assume an elongated shape with stress-fibers, redistribution of SNAI1 and VIM, and disappearance of CDH1 staining, consistent with our previous experiments (FIG. 9A). By contrast, JQ1 blocked TGFβ-induced stress fiber formation, acquisition of elongated shape, and upregulation and cytosolic redistribution of SNAI1 and VIM (FIG. 9A). JQ1 treatment also maintained the expression and cellular distribution of CDH1 (FIG. 9A). Separately, RNAs harvested from a 15 d time course experiment were assayed by Q-RT-PCR for core EMT transcription factors, and mesenchymal and NFκB-dependent genes. The inventors found that JQ1 significantly blocked TGFβ-induced expression of SNAI1, ZEB1, FN1, VIM, as well as that of IL-6 mRNA in hSAECs (FIG. 9B). By contrast, JQ1 partially maintained CDH1 expression, but not to levels seen in normal hSAECs (FIG. 9B).

Figure 13:
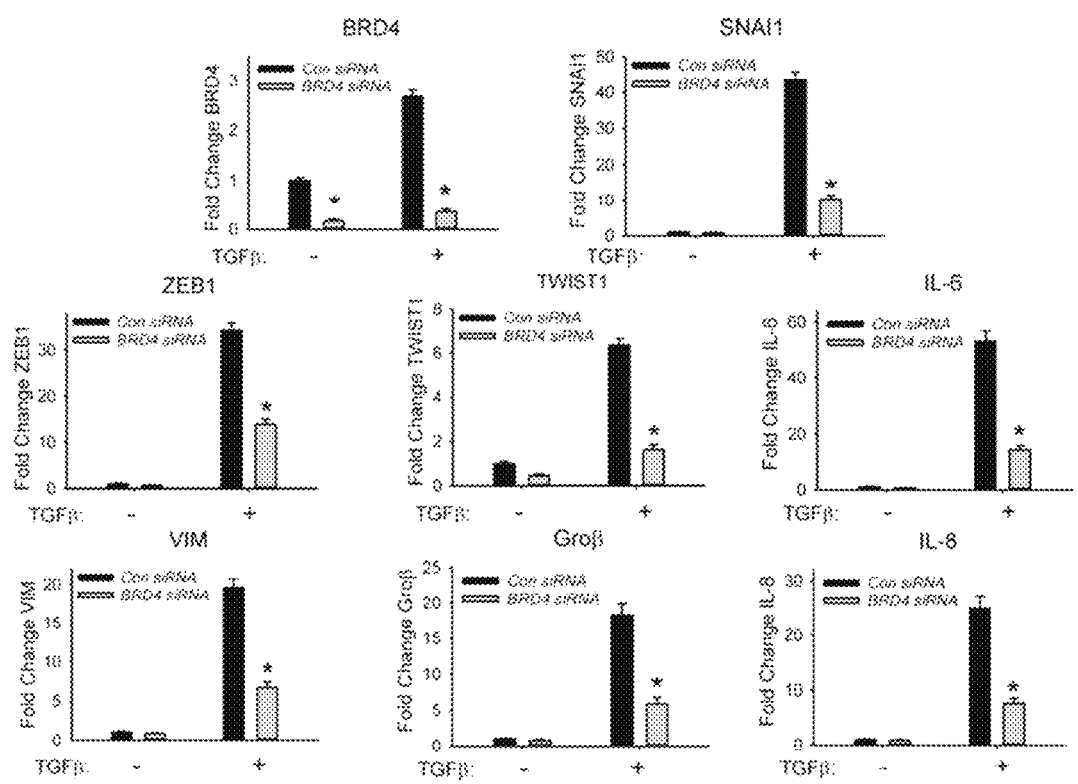
FIG. 13. BRD4 depletion blocks TGFβ-induced EMT gene expression. Control or BRD4-specific siRNAs were reverse-transfected into hSAECs. The RNA samples were examined for the expression of BRD4, SNAI1 ZEB1, TWIST1, VIM, and IL-6 mRNA by Q-RT-PCR. Tukey's post hoc test was performed to determine significance. *=p<0.05 compared to control siRNA. The data are the means±S.D. from n=3 experiments.

As an independent approach, the inventors evaluated the effect of BRD4 depletion on the TGFβ-induced EMT. Control or BRD4-specific siRNAs were reverse-transfected into hSAECs, producing an 85% inhibition of BRD4 expression in the absence or presence of TGFβ stimulation (FIG. 13). Consistent with the results with JQ1, it was found that siRNA-mediated BRD4 depletion also significantly inhibited the TGFβ-induced enhancement of SNAI1, ZEB1, FN, VIM and IL-6 expression (FIG. 13). Together, these results strongly suggest the requirement for BRD4 in the initiation and maintenance of the NFκB-dependent EMT in hSAECs.

Figure 10A:
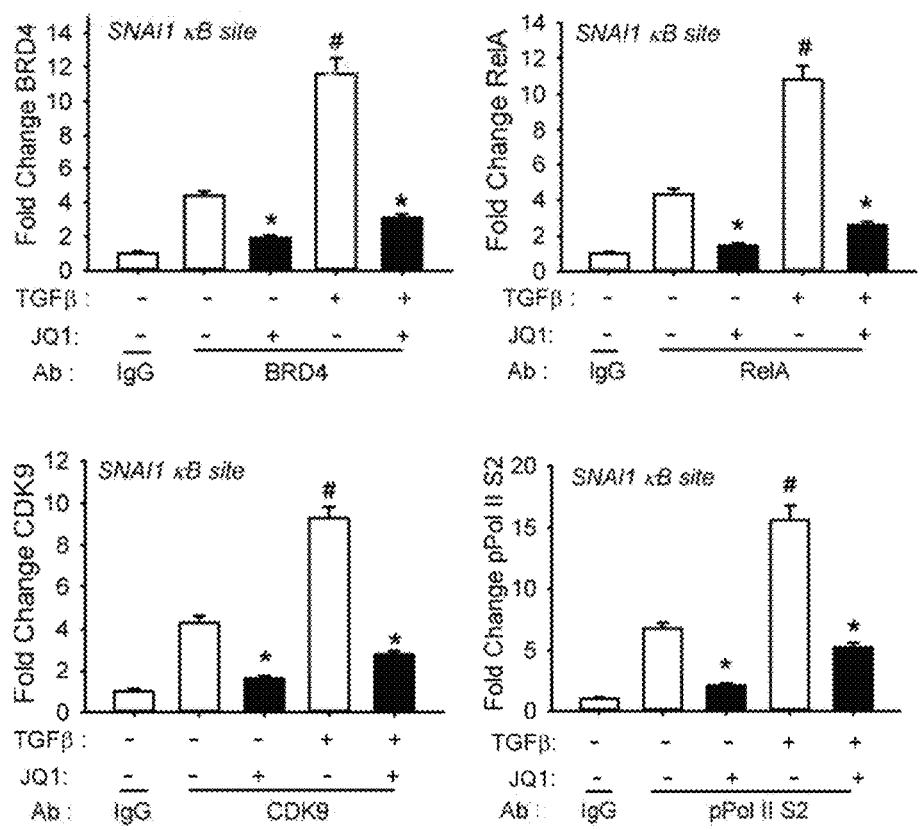
FIG. 10A-10D. XChIP analysis of NF-B binding sites of EMT genes under BRD4 inhibition. hSAECs were treated with TGFβ for 0 or 15 days±JQ1, and chromatin crosslinked and subjected to IP with Abs specific for RelA, CDK9, BRD4, or phospho-Ser2 CTD RNA Pol II. Anti-rabbit IgG was used as the negative control. The recruitment of RelA, CDK9, BRD4, and phospho-Ser2 CTD RNA Pol II to the SNAI1 (A), ZEB1 (B), IL-6 (C), and VIM (D) promoters was determined by Q-gPCR. Tukey's post hoc test was performed to determine significance. *=p <0.05 compared to without JQ1 and #=p<0.05 compared to without TGFβ. The data are the means±S.D. from n=3 experiments.
Figure 10B:
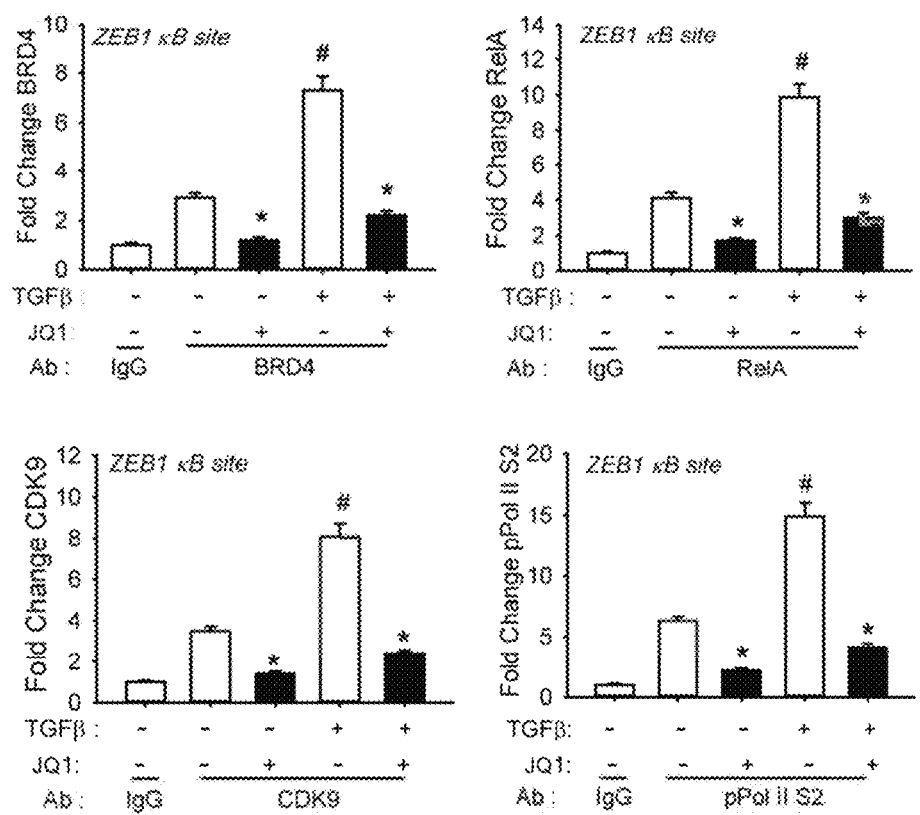
Figure 10C:
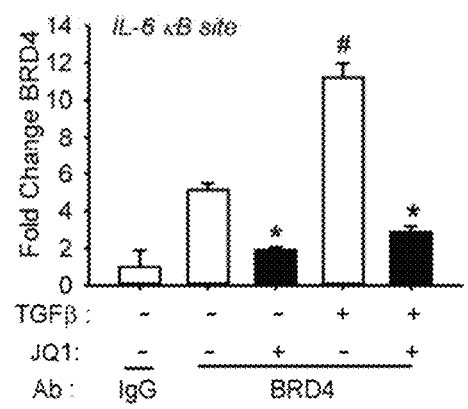
Figure 10C:
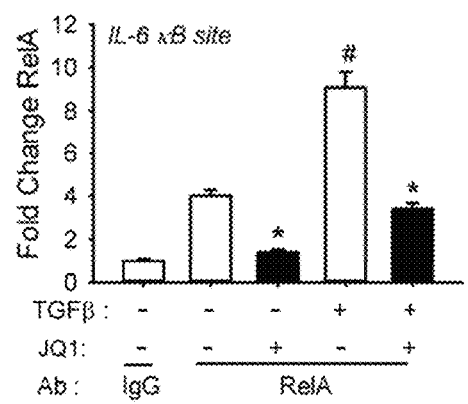
Figure 10C:
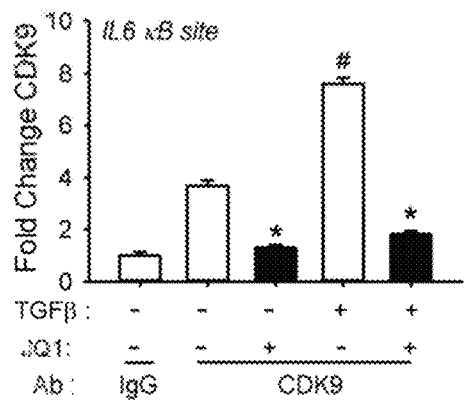
Figure 10C:
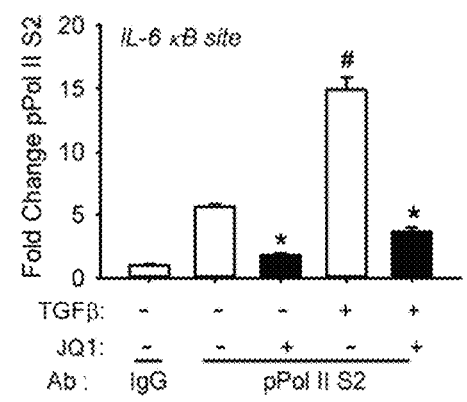
Figure 10D:
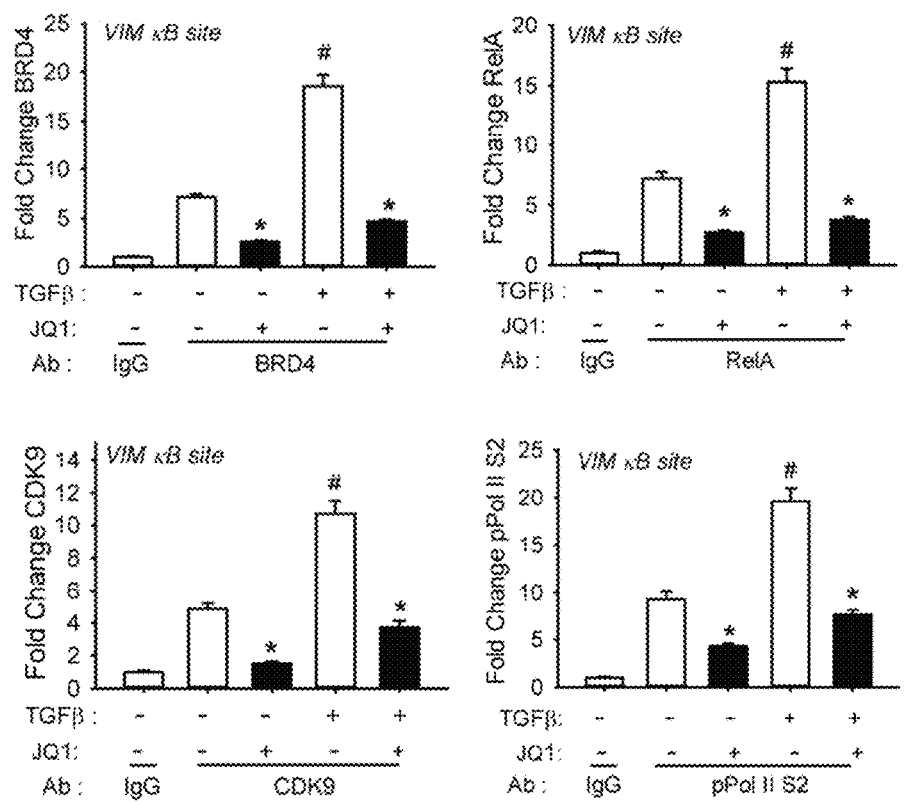

BRD4 binding stabilizes NFκB and transcriptional elongation complex assembly for initiation of the type II EMT and transcriptional reprogramming. BRD4 plays a major role in stabilizing CDK9 binding to acetylated histone H4-enriched chromatin. To determine whether BRD4 is involved in stabilizing the TGFβ-induced NFκB complex, the inventors examined the effect of JQ1 on recruitment of the RelA·CDK9 complex in the TGFβ-induced EMT. hSAECs treated in the absence or presence of JQ1 were or were not stimulated with TGFβ and subjected to XChIP. Chromatin was IPed with anti-RelA, -CDK9, -BRD4, and -phospho-Ser 2 CTD RNA Pol II-specific Abs. It was found that the TGFβ-induced recruitment of BRD4 to the 5'NFκB site of SNAI1 was significantly attenuated, as expected (FIG. 10A). The inventors also examined the effects of BRD4 inhibition on RelA, CDK9, and phospho-Ser 2 CTD RNA Pol II recruitment to SNAI1; all were significantly disrupted (FIG. 10A). Similar findings were observed for the ZEB1, IL-6, and VIM promoters (FIG. 10B, 10C, and 10D). Together, these results support the idea that BRD4 recruitment stabilizes RelA-dependent assembly of the transcriptional elongation complex required for phospho-Ser 2 CTD RNA Pol II formation, providing its mechanism for transcriptional reprogramming in the type II EMT.

Figure 11A:
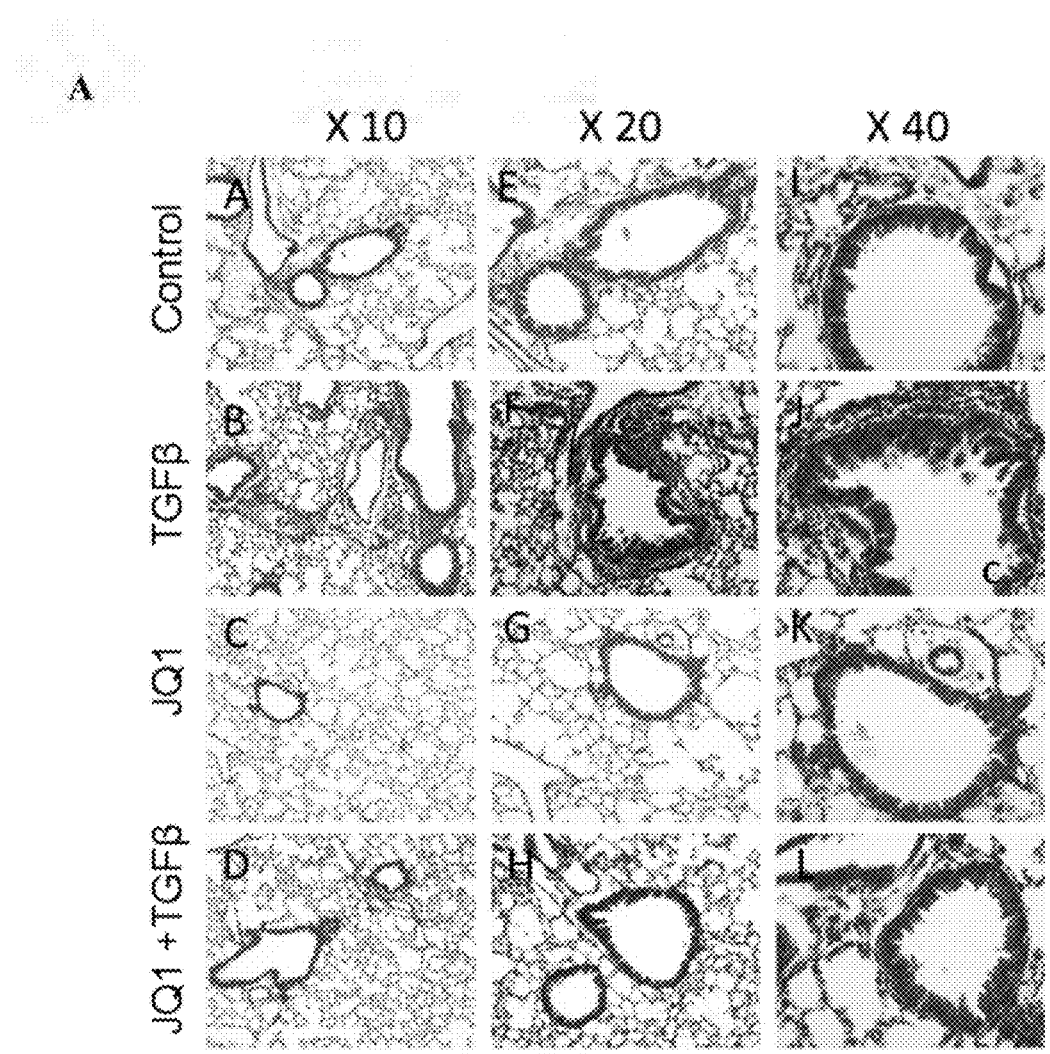
FIG. 11A-11C. BRD4 mediates TGFβ-induced pulmonary fibrosis in mice. 15-week-old C57B6 mice were pre-treated ±JQ1 (100 mg/kg body weight, i.p.) and given multiple intranasal challenges with TGFβ (1 μg/mouse every other days for 30 d). (A) Morphological changes after Masson Trichrome staining. C57/BL6 mice were chronically treated in the absence (A and C) or presence of TGFβ (B and D). Two groups of mice were treated with JQ1 (100 mg/kg, C and D). The images were taken at magnification of 10 (A-A, A-B, A-C, and A-D), 20 (A-E, A-F, A-G, and A-H), and 40 (A-I, A-J, A-K, and A-L) times, respectively. (B) The level of lung fibrosis was assessed using the Ashcroft scoring method. *=p<0.05 compared to without JQ1 and #=p<0.05 compared to without TGFβ. (C) Changes in fibrotic program. Q-RT-PCR for mCol1A1, mFN1, mSNAI1, mVIM, mαSMA, and mIL-6 mRNA was performed in lungs from the same experiment. Tukey's post hoc test was performed to determine significance. Tukey's post hoc test was performed to determine significance. *=p<0.05 compared to without JQ1.
Figure 11B:
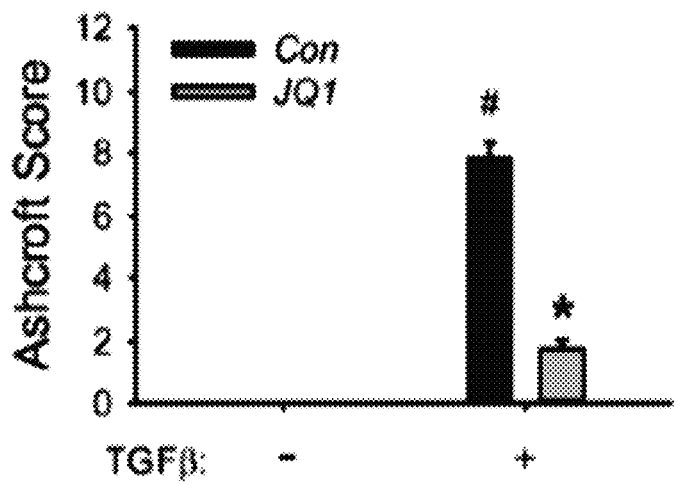
Figure 14A:
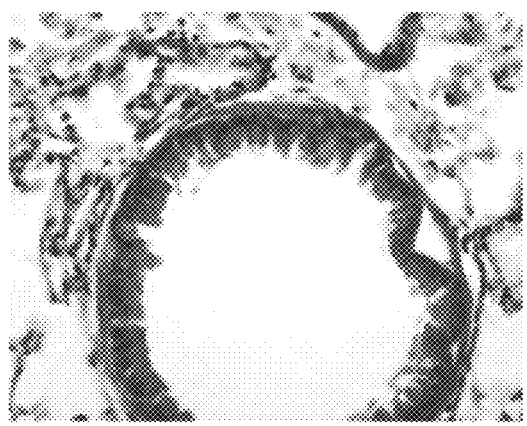
FIG. 14A-14C. Morphological changes in airway histology. Chronic TGFβ-treated airways were subjected to Masson Trichrome staining. TGFβ-induced marked accumulation of fibrosis (B), disruption of the epithelial layer, and alveolar thickening (B). Concomitant treatment with JQ1 effectively blocked TGFβ-induced airway fibrosis (C). PBS treatment as mock group (A). Magnification=40X.
Figure 14B:
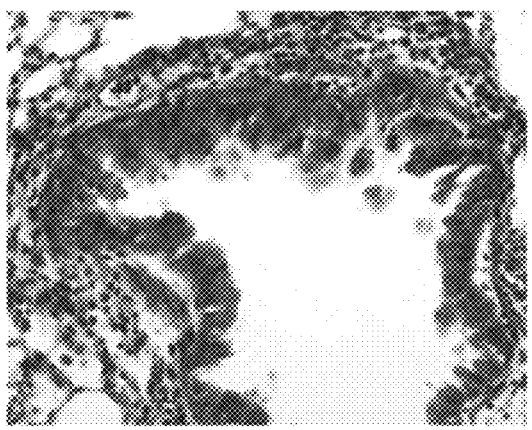
Figure 14C:
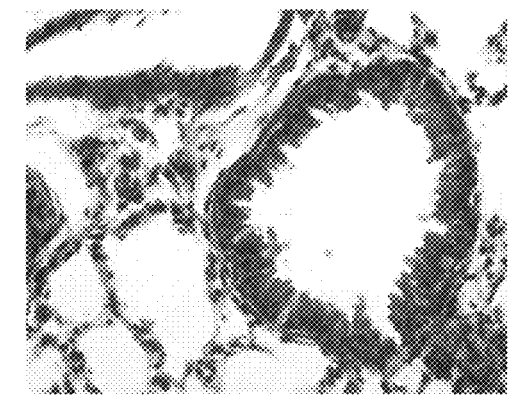

BRD4 mediates chronic TGFβ treatment-induced pulmonary fibrosis in vivo. It is well established that TGFβ plays a central role in the development of pulmonary fibrosis (Broekelmann et al., 1991, PNAS U. S. A. 88:6642-46; Fernandez and Eickelberg, 2012, Proc. Am. Thorac. Soc. 9:111-16), as TGFβ overexpression is sufficient to induce the formation of pulmonary fibrosis in rodents (Sime et al., 1997, J, Clin. Invest. 100:768-76; Warshamana et al., 2002, Int. I Exp. Pathol. 83:183-201). To establish the role of the NFκB-BRD4 pathway in the development of airway fibrosis in vivo, the effect of JQ1 in a mouse model of TGFβ-induced fibrosis was evaluated. C57BL6/J mice±JQ1 treatment were given repetitive intranasal challenge with TGFβ to induce chronic fibrosis. It was found that chronic treatment of TGFβ in the airways of control mice induced marked accumulation of subepithelial fibrosis with enhanced collagen distribution throughout the parenchyma (FIG. 11A, panel J and FIG. 14B). The epithelium was hypertrophic, and there was thickening of the alveolar septae (FIG. 11A, panels B, F, and J, FIG. 11B, and FIG. 14B). By contrast, the lungs of animals treated with JQ1 were histologically normal, indicating that JQ1 effectively blocks TGFβ-induced airway fibrosis (FIG. 11A, panels D, H, and L, FIG. 11B, and FIG. 14C). To assess the levels of pulmonary fibrosis in each treatment group, pulmonary fibrosis was graded using the Ashcroft scoring method (Hubner et al., 2008, Biotechniques. 44:507) (FIG. 11B). The average combined Ashcroft score in mice with chronic TGFβ treatment was 8, indicating a moderate level of pulmonary fibrosis, while the combined Ashcroft score in JQ1 mice with chronic TGFβ treatment was significantly lower (FIG. 11B). The results indicating that the BRD4 inhibitor JQ1 effectively blocks chronic TGFβ treatment-induced airway fibrosis not only demonstrate the determining role of BRD4 in the development of airway remodeling, but also provide a new approach to therapeutic intervention for chronic airway disease-associated pulmonary fibrosis.

Figure 11C:
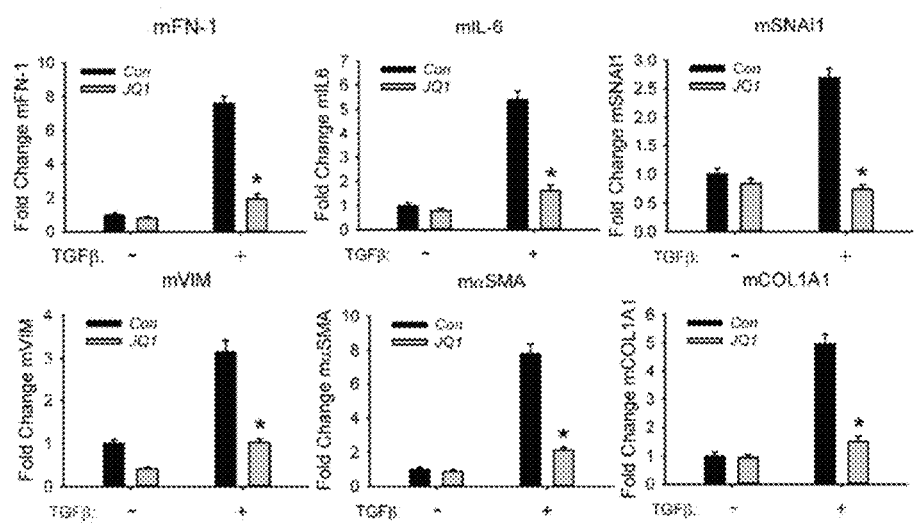
Figure 12A:
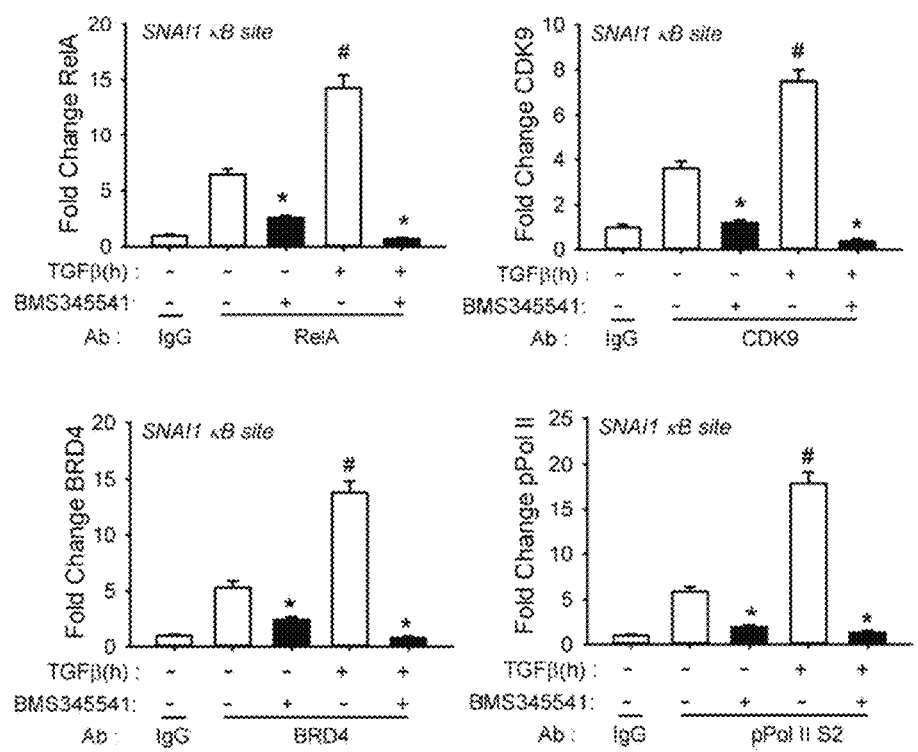
FIG. 12A-12D. Effect of an IKK inhibitor on transcriptional elongation complex formation on EMT core regulator genes. hSAECs were stimulated with TGFβ for 0 or 15±BMS-345541. Shown is an XCHIP assay for chromatin IPed with Abs specific for RelA, CDK9, BRD4, or phospho-Ser2 CTD Pol II. Anti-rabbit IgG was used as the negative control. The recruitment of RelA, CDK9, BRD4, and pSer2 Pol II to the 5' NFκB site in the EMT gene promoters for SNAI1 (A), ZEB1 (B), IL-6 (C), and VIM (D) were determined by Q-gPCR. Tukey's post hoc test was performed to determine significance. *=p<0.05 compared to without doxycycline. #=p<0.05 compared to mock treatment. The data are from three independent experiments.
Figure 12B:
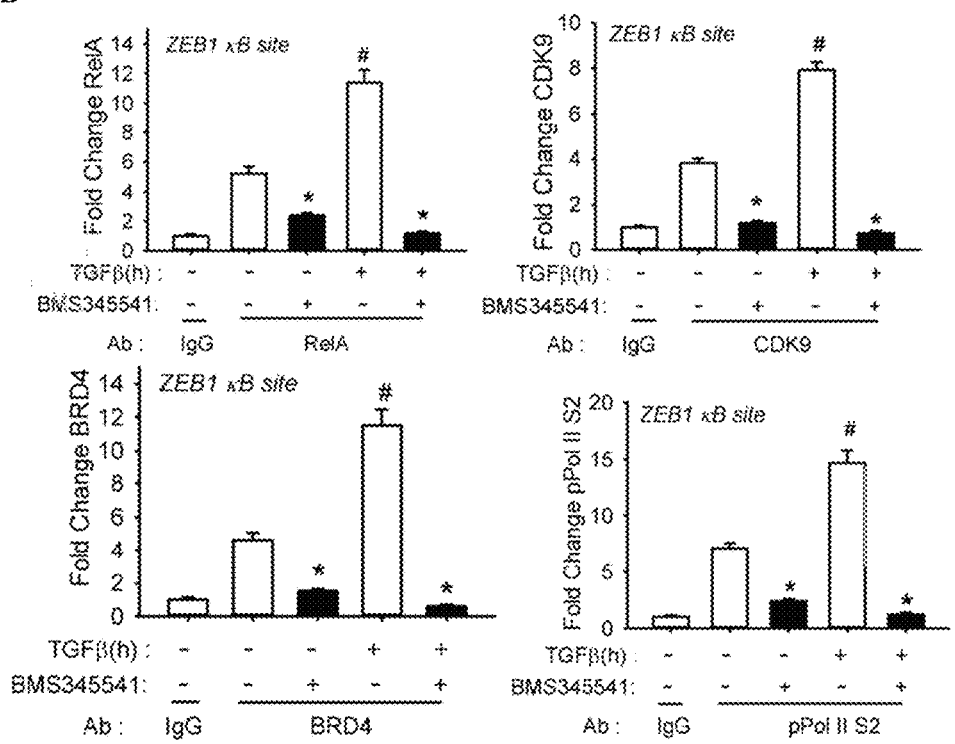
Figure 12C:
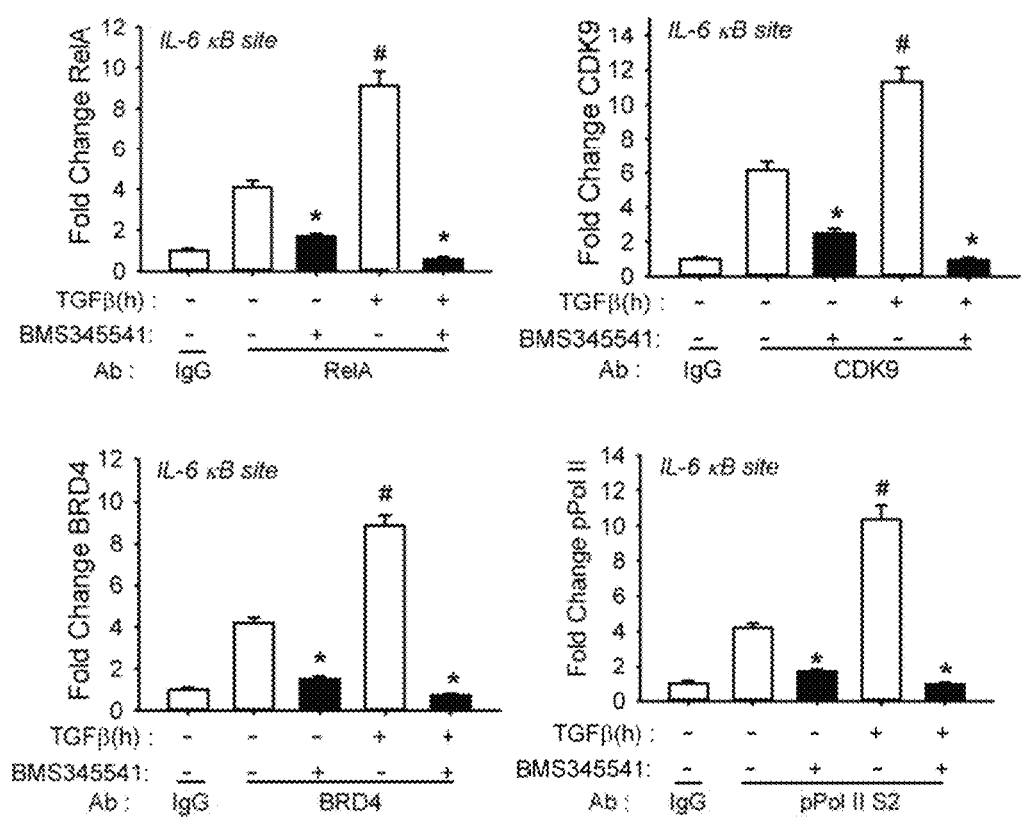
Figure 12D:
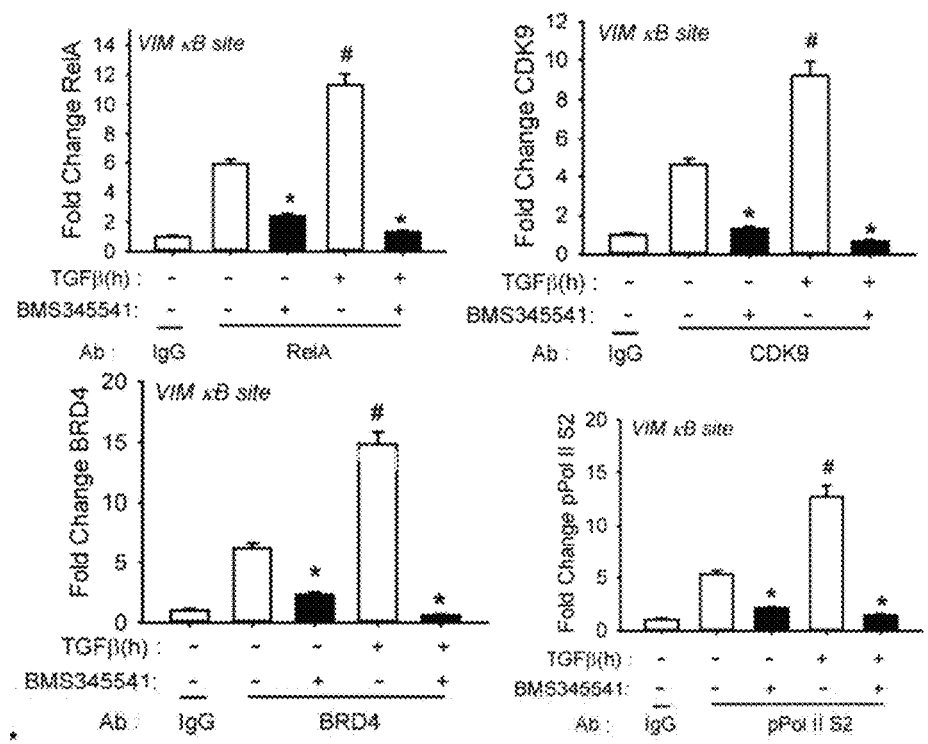

At the molecular level, repetitive TGFβ stimulation induced the expression of mSNAI1, mesenchymal genes (mFN-1, maSMA, mCol1A1) and NFκB/RelA-dependent mIL-6 genes (assessed by Q-RT-PCR; FIG. 11C). JQ1 treatment significantly inhibited this TGFβ-induced pulmonary fibrotic program (FIG. 11C). Together the mechanistic studies both in vitro and in vivo have identified BRD4 as a key epigenetic regulator of TGFβ-induced airway remodeling, where its inhibition reduces airway fibrosis and remodeling.

Materials and Methods hSAECs culture and induction of the EMT transformation. An immortalized human small airway epithelial cell (hSAEC) line established by infecting primary hSAECs with human telomerase (hTERT) and cyclin-dependent kinase (CDK)-4 retrovirus constructs was obtained from John Minna, UTSW (Ramirez et al., 2004, Cancer. Res. 64:9027-34). The immortalized hSAECs were grown in SAGM small airway epithelial cell growth medium (Lonza, Walkersville, MD) in a humidified 5% $CO_2$ atmosphere. For induction of the EMT, hSAECs were TGFIβ-stimulated for 15 d (10 ng/ml, PeproTech, Rocky Hill, NJ). The small-molecule IKK inhibitor BMS345541 was purchased from Sigma Aldrich and used at 10 μM (Burke et al., 2003, J. Biol. Chem. 278:1450-56). The small-molecule BRD4 inhibitor JQ1 was purchased from Cayman Chemical (Ann Arbor, Mich.) and used at 10 μM (Filippakopoulos et al., 2010, Nature. 468: 1067-73).

Immunostaining and Confocal Immunofluorescence Microscopy. hSAECs were incubated±TGFβ (10 ng/mL) for 15 days, re-plated on glass cover slips pretreated with rat tail collagen (Roche Applied Sciences), and fixed with 4% paraformaldehyde in PBS. Afterwards, the fixed cells were stained with Alexa Fluor® 568 phalloidin (Life Technologies) for cytoplasmic distribution of F-actin and also counterstained with 4', 6-diamidino-2-phenylindole (DAPI) for nuclear staining. The cells were visualized with a Nikon fluorescence confocal microscope at a magnification of 63×.

For immunofluorescence staining, hSAECs were plated on rat tail collagen-treated cover glasses and stimulated for the indicated times. The cells were fixed with 4% paraformaldehyde in PBS and incubated with 0.1 m ammonium chloride for 10 min. Cells were permeabilized with 0.5% Triton-100, followed by incubation in blocking buffer (5% goat serum, 0.1% IGEPAL CA-630, 0.05% $NaN_3$, and 1% BSA) and incubated with anti-SNAIL1, anti-E-Cadherin, and anti-vimentin antibodies (Abs; Abcam, Santa Cruz, Calif.) incubation buffer (0.1% IGEPAL CA-630, 0.05% $NaN_3$, and 2% BSA) overnight at 4° C. After washing, cells were stained with Alexa Fluor 488-conjugated goat anti-rabbit IgG (Life Technologies) in incubation buffer for 1 h, then visualized with a Nikon fluorescence confocal microscope, magnification 63×.

RelA shRNA and control shRNA stable hSAECs. The TRIPZ Tet-on inducible lentiviral RelA shRNA and related constructs were obtained commercially (Dharmacon, ThermoFisher Scientific, Lafayette, Colo.). To generate viruses, these constructs along with a packaging construct were reverse-transfected into BOS23 cell lines per the vendor's instructions. The virus-containing conditioned medium was collected and later used to infect hSAECs. 72 hours after virus infection, 4 μg/ml of puromycin was added to the culture medium of infected hSAECs for antibiotic selection. 5 to 8 weeks after adding puromycin, the puromycin-resistant hSAECs stably expressing RelA shRNA (and empty vector shRNA controls) were harvested and later characterized for inducible RelA depletion under 2 μg/ml doxycycline.

Reverse siRNA transfection. Control and BRD4 siRNAs (Dharmacon, ThermoFisher Scientific, Lafayette, Colo. ) were reverse-transfected by plating trypsinized hSAECs into a dish containing 100 nM siRNA-TranslT-siQUEST complexes (Mirus Bio Corp). At the indicated times, cells were washed with phosphate-buffered saline (PBS) twice and lysed in TRI reagent (Sigma-Aldrich).

Subcellular fractionation and Western immunoblot analyses. Nuclear and cytoplasmic proteins were fractionated as previously described (Brasier et al., 2011, *J. Virol.* 85:11752-69; Hu et al., 2013, *Int. I Mol. Med.* 32:347-54). For Western blots, equal amounts of nuclear protein were fractionated by SDS-PAGE and transferred to PVDF membranes. The membranes were incubated with affinity purified rabbit polyclonal Abs to RelA (Santa Cruz Biotechnology). Washed membranes were then incubated with IRDye 800-labeled anti-rabbit IgG Abs (Rockland Immunochemicals, Gilbertsville, Pa.), and immune complexes quantified using the Odyssey Infrared Imaging system (LICOR Biosciences, Lincoln, Nebr.).

Quantitative real-time reverse transcription-PCR (Q-RT-PCR). Total RNA was extracted using acid guanidinium phenol extraction (Tri Reagent; Sigma). For gene expression analyses, 1 μg of RNA was reverse-transcribed using SuperScript III in a 20-μl reaction mixture. The rest of the procedures were as described previously (Brasier et al., 2011, *J. Virol.* 85:11752-69). The forward and reverse gene-specific Q-RT-PCR primers are listed in Table 1; relative changes in gene expression were quantified using the ΔΔCT method.

Dual cross-link chromatin immunoprecipitation (XChIP). XChIP was performed as described previously (Nowak et al., 2005, *Biotechniques.* 39:715-25). hSAECs ($4 \times 10^6$ to $6 \times 10^6$ per 100-mm dish) were washed twice with PBS. Protein-protein cross-linking was first performed with disuccinimidyl glutarate (2mM, Pierce), followed by protein-DNA cross-linking with formaldehyde. Equal amounts of sheared chromatin were immunoprecipitated overnight at 4° C. with 4 μg of the indicated Ab in ChIP dilution buffer (Tian et al., 2012, *Methods. Mol. Biol.* 809:105-20). Immunoprecipitates were collected with 40 μL protein A magnetic beads (Dynal Inc.), washed, and eluted in 250 μL elution buffer for 15 min at room temperature. Samples were de-cross-linked in 0.2 M NaCl at 65° C. for 2 h. The precipitated DNA was phenol/chloroform-extracted, precipitated with 100% ethanol, and dried.

Quantitative real time genomic PCR (Q-gPCR). Gene enrichment in XChIP was determined by Q-gPCR using region-specific PCR primers (Table 2). Standard curves were generated using a dilution series of genomic DNA (from 1 ng to 100 ng) for each primer pair. The fold change of DNA in each immunoprecipitate was determined by normalizing the absolute amount to the input DNA reference and calculating the fold change relative to that amount in unstimulated cells.

Immunoprecipitation (IP). hSAECs ($4 \times 10^6$ to $6 \times 10^6$ per 100-mm dish) were washed twice with PBS. Protein-protein cross-linking was first performed with disuccinimidyl glutarate. The cross-linked cells were then collected into Eppendorf tubes and washed twice with PBS. After washing, the cells were suspended in RIPA buffer with complete protease inhibitor cocktail [Sigma Aldrich] and 0.1% IGEPAL CA-630 (MP Biomedicals) and incubated on ice for 30 m. After incubation, the cells were sonicated 4 times and centrifuged at 12,000×g for 10 m. The supernatants were collected and their protein concentrations quantified. Equal volumes of whole-cell lysates were IPed overnight at 4° C. with 4 μg of the Anti-RelA and Anti-BRD4 Abs (Santa Cruz) in ChIP dilution buffer (Tian et al., 2013, *J. Virol.* 87:7075-92). IPs were collected with 40 μL protein A magnetic beads (Dynal Inc.). The samples were de-associated with beads and prepared for SID-SRM-MS analysis.

TGFβ-induced pulmonary fibrosis in mice. Male C57BL6/J mice aged 15 weeks were purchased from The Jackson Laboratory (Bar Harbor, Me.) and housed under pathogen-free conditions with food and water ad libitum. Mice were given multiple challenges with 1 μg/mouse of TGFβ every other day for a total of 15 TGFβ treatments. Meanwhile, mice were pre-treated with or without JQ1 (50 mg/kg body weight, i.p.) before TGFβ administration. Ten days after the last TGFβ treatment, bronchoalveolar lavages were obtained for quantifying innate immune cells and measuring cytokine and chemokine secretion; the mice were sacrificed and lung tissues taken for RNA extraction and fixed for histological examination. Whole lungs were inflated under 25 cm $H_2O$ pressure with 10% (v/v) neutral buffered formalin through the tracheal cannula and immersed in formalin for at least 24 hours. After being processed into paraffin blocks, the lungs were cut into 5-μm sections and stained either with Masson Trichrome or H&E to assess fibrotic changes in the lungs.

Assessment of levels of pulmonary fibrosis. Pulmonary fibrosis was graded using the Ashcroft scoring method as described (Hubner et al., 2008, *Biotechniques.* 44:507). In brief, to determine the fibrosis histopathology score for the lung of each mouse, the entire left and right longitudinal lung sections were scored separately (score range, 0 to 9) at ×100 magnification, and the scores were combined (total score range, 0 to 18). Grades 2, 4, 6, and 8 were intermediate grades assigned on the basis of the predominant histology changes if features described for two distinct grades (as described) were present in the section, to account for the progressive nature of the fibrotic lesion.

Stable isotope dilution (SID)-selected Reaction Monitoring (SRM)-mass spectrometry (MS). The selection of the signature peptides for targeted MS-based quantification of RelA, CDK9 and BRD4 used a workflow described in previous publications (Zhao et al., 2013, *Mol. Cell. Proteomics.* 12:1513-29; Zhao et al., 2011, *Mol. Cell. Proteomics.* 10:M111). The signature peptides and SRM parameters are listed in Table 3. The peptides were chemically synthesized incorporating isotopically labeled [$^{13}C_6{}^{15}N_4$] Arginine or [$^{13}C_6{}^{15}N_2$] Lysine to a 99% isotopic enrichment (Thermo Scientific).

TABLE 3

SRM parameters of SRM assays of proteins for sample amount normalization. Masses listed are for the native forms of the peptides.

| Gene Name | Swissprot No | Sequence | Q1 m/z | Q3 m/z | Ion type | CE (V) |
|---|---|---|---|---|---|---|
| RelA | Q04206 | TPPYADPSLQAPVR (SEQ ID NO: 57) | 756.396 | 867.504 | y4 | 30 |
| | | | 756.396 | 982.531 | y5 | 24 |
| | | | 756.396 | 1053.568 | y6 | 26 |
| | | | 756.396 | 1313.684 | y7 | 26 |
| | | | 717.938 | 782.513 | y7 | 27 |

TABLE 3-continued

SRM parameters of SRM assays of proteins for sample amount normalization. Masses listed are for the native forms of the peptides.

| Gene Name | Swissprot No | Sequence | Q1 m/z | Q3 m/z | Ion type | CE (V) |
|---|---|---|---|---|---|---|
| BRD4 | O60885 | AASVVQPQPLVVVK (SEQ ID NO: 58) | 717.938 | 879.566 | y8 | 27 |
|  |  |  | 717.938 | 1007.624 | y9 | 27 |
|  |  |  | 717.938 | 1106.693 | y10 | 27 |
| CDK9 | P50750 | DPYALDLIDK (SEQ ID NO: 59) | 581.803 | 603.334 | y5 | 23 |
|  |  |  | 581.803 | 716.418 | y6 | 23 |
|  |  |  | 581.803 | 787.455 | y7 | 23 |
|  |  |  | 581.803 | 950.519 | y8 | 23 |

Abbreviations: CE, collision energy; Q, quadrupole.

The proteins were IPed with specific Abs and captured on protein A magnetic beads (Dynal Inc.). The proteins on the beads were digested with trypsin. After trypsin digestion, an aliquot of 5 µL of stable isotope-labeled signature peptides was added to each tryptic digest. These samples were desalted with ZipTip C18 before MS analysis. SRM assays of RelA, BRD4 and CDK9 were performed. The signature peptides of RelA phospho-Ser276, RPS [phosphoryl] DR (m/z 355.653), was used for parallel reaction monitoring (PRM)-MS analyses. All peptide samples were separated on an online nanoflow Easy nLC1000 UHPLC system (Thermo Scientific) and analyzed on the Q Exactive Orbitrap mass spectrometer (Thermo Scientific, San Jose, Calif.). The acquisition employed an Orbitrap resolution of 35,000 (@m/z 200), a target AGC value of 2e5, and maximum fill times of 100 ms. PRM targeted the native and stable isotope labeled signature peptide of RelA phospho-Ser276.

Statistical analysis. One-way analysis of variance (ANOVA) was performed when looking for time differences, followed by Tukey's post hoc test to determine significance. Mann-Whitney tests were used for nonparametric data. A P value of <0.05 was considered significant (Tian et al., J Virol, 2013, 87(12):7075-92).

The invention claimed is:

1. A method of treating epithelial-mesenchymal transition (EMT) lung fibrosis in a subject comprising administering a therapeutically effective amount of a small molecule BRD4 inhibitor to a subject having or at risk of developing EMT lung fibrosis.

2. The method of claim 1, wherein the BRD4 inhibitor is administered by inhalation or instillation.

3. The method of claim 1, wherein the BRD4 inhibitor is administered at a dose of 150 to 500 mg/day.

4. The method of claim 1, wherein the BRD4 inhibitor is JQ1.

* * * * *

SEQUENCE LISTING

<160> NUMBER OF SEQ ID NOS: 59

<210> SEQ ID NO 1
<211> LENGTH: 20
<212> TYPE: DNA
<213> ORGANISM: Artificial Sequence
<220> FEATURE:
<223> OTHER INFORMATION: Synthetic Primer

<400> SEQUENCE: 1
ccggaccgct gcatccacag            20

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
agtccccacg ctgctcttct            20

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
acctccaacc ctaacaagcc            20

<210> SEQ ID NO 4
<211> LENGTH: 22

```
<212> TYPE: DNA
<213> ORGANISM: Artificial Sequence
<220> FEATURE:
<223> OTHER INFORMATION: Synthetic Primer

<400> SEQUENCE: 4
tttccatagt gtcttgagca cc                                          22

<210> SEQ ID NO 5
<211> LENGTH: 19
<212> TYPE: DNA
<213> ORGANISM: Artificial Sequence
<220> FEATURE:
<223> OTHER INFORMATION: Synthetic Primer

<400> SEQUENCE: 5
cggtggctgt cagtcaaag                                              19

<210> SEQ ID NO 6
<211> LENGTH: 21
<212> TYPE: DNA
<213> ORGANISM: Artificial Sequence
<220> FEATURE:
<223> OTHER INFORMATION: Synthetic Primer

<400> SEQUENCE: 6
aaacctcggc ttcctccata a                                           21

<210> SEQ ID NO 7
<211> LENGTH: 23
<212> TYPE: DNA
<213> ORGANISM: Artificial Sequence
<220> FEATURE:
<223> OTHER INFORMATION: Synthetic Primer

<400> SEQUENCE: 7
ccagaagaac tggtacatca gca                                         23

<210> SEQ ID NO 8
<211> LENGTH: 21
<212> TYPE: DNA
<213> ORGANISM: Artificial Sequence
<220> FEATURE:
<223> OTHER INFORMATION: Synthetic Primer

<400> SEQUENCE: 8
cgccatactc gaactggaat c                                           21

<210> SEQ ID NO 9
<211> LENGTH: 23
<212> TYPE: DNA
<213> ORGANISM: Artificial Sequence
<220> FEATURE:
<223> OTHER INFORMATION: Synthetic Primer

<400> SEQUENCE: 9
ctggattcaa tgaggagact tgc                                         23

<210> SEQ ID NO 10
<211> LENGTH: 27
<212> TYPE: DNA
<213> ORGANISM: Artificial Sequence
<220> FEATURE:
<223> OTHER INFORMATION: Synthetic Primer

<400> SEQUENCE: 10
```
tcaaatctgt tctggaggta ctctagg                                           27

<210> SEQ ID NO 11
<211> LENGTH: 19
<212> TYPE: DNA
<213> ORGANISM: Artificial Sequence
<220> FEATURE:
<223> OTHER INFORMATION: Synthetic Primer

<400> SEQUENCE: 11
gcgctctttc ctcgtcagg                                                    19

<210> SEQ ID NO 12
<211> LENGTH: 22
<212> TYPE: DNA
<213> ORGANISM: Artificial Sequence
<220> FEATURE:
<223> OTHER INFORMATION: Synthetic Primer

<400> SEQUENCE: 12
gggctgctgg aaggtaaact ct                                                22

<210> SEQ ID NO 13
<211> LENGTH: 19
<212> TYPE: DNA
<213> ORGANISM: Artificial Sequence
<220> FEATURE:
<223> OTHER INFORMATION: Synthetic Primer

<400> SEQUENCE: 13
tctcggtctg gaggatgga                                                    19

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14
caatgacatc taggtctccg                                                   20

<210> SEQ ID NO 15
<211> LENGTH: 22
<212> TYPE: DNA
<213> ORGANISM: Artificial Sequence
<220> FEATURE:
<223> OTHER INFORMATION: Synthetic Primer

<400> SEQUENCE: 15
gctcaatgtt aagatggccc tt                                                22

<210> SEQ ID NO 16
<211> LENGTH: 22
<212> TYPE: DNA
<213> ORGANISM: Artificial Sequence
<220> FEATURE:
<223> OTHER INFORMATION: Synthetic Primer

<400> SEQUENCE: 16
tggaagaggc agagaaatcc tg                                                22

<210> SEQ ID NO 17
<211> LENGTH: 23
<212> TYPE: DNA
<213> ORGANISM: Artificial Sequence

```
<220> FEATURE:
<223> OTHER INFORMATION: Synthetic Primer

<400> SEQUENCE: 17
gatgatgaat gcgagtcaga tgc                                        23

<210> SEQ ID NO 18
<211> LENGTH: 23
<212> TYPE: DNA
<213> ORGANISM: Artificial Sequence
<220> FEATURE:
<223> OTHER INFORMATION: Synthetic Primer

<400> SEQUENCE: 18
gatgatgaat gcgagtcaga tgc                                        23

<210> SEQ ID NO 19
<211> LENGTH: 25
<212> TYPE: DNA
<213> ORGANISM: Artificial Sequence
<220> FEATURE:
<223> OTHER INFORMATION: Synthetic Primer

<400> SEQUENCE: 19
aagacatact ccaaacctttt ccacc                                     25

<210> SEQ ID NO 20
<211> LENGTH: 22
<212> TYPE: DNA
<213> ORGANISM: Artificial Sequence
<220> FEATURE:
<223> OTHER INFORMATION: Synthetic Primer

<400> SEQUENCE: 20
caataatttc tgtgttggcg ca                                         22

<210> SEQ ID NO 21
<211> LENGTH: 20
<212> TYPE: DNA
<213> ORGANISM: Artificial Sequence
<220> FEATURE:
<223> OTHER INFORMATION: Synthetic Primer

<400> SEQUENCE: 21
cacactcaag aatgggcaga                                            20

<210> SEQ ID NO 22
<211> LENGTH: 20
<212> TYPE: DNA
<213> ORGANISM: Artificial Sequence
<220> FEATURE:
<223> OTHER INFORMATION: Synthetic Primer

<400> SEQUENCE: 22
gcttcctcct tccttctggt                                            20

<210> SEQ ID NO 23
<211> LENGTH: 22
<212> TYPE: DNA
<213> ORGANISM: Artificial Sequence
<220> FEATURE:
<223> OTHER INFORMATION: Synthetic Primer

<400> SEQUENCE: 23
tcctcaggct ttgtatttga gc                                         22
```

<210> SEQ ID NO 24
<211> LENGTH: 22
<212> TYPE: DNA
<213> ORGANISM: Artificial Sequence
<220> FEATURE:
<223> OTHER INFORMATION: Synthetic Primer

<400> SEQUENCE: 24
tgtgtatcgg tgcatggttt ta                                          22

<210> SEQ ID NO 25
<211> LENGTH: 23
<212> TYPE: DNA
<213> ORGANISM: Artificial Sequence
<220> FEATURE:
<223> OTHER INFORMATION: Synthetic Primer

<400> SEQUENCE: 25
ctccgagact tcgaggaaa tac                                          23

<210> SEQ ID NO 26
<211> LENGTH: 23
<212> TYPE: DNA
<213> ORGANISM: Artificial Sequence
<220> FEATURE:
<223> OTHER INFORMATION: Synthetic Primer

<400> SEQUENCE: 26
gccattgtag ttggtagcct tca                                         23

<210> SEQ ID NO 27
<211> LENGTH: 20
<212> TYPE: DNA
<213> ORGANISM: Artificial Sequence
<220> FEATURE:
<223> OTHER INFORMATION: Synthetic Primer

<400> SEQUENCE: 27
cgagagctac acgttcacgg                                             20

<210> SEQ ID NO 28
<211> LENGTH: 21
<212> TYPE: DNA
<213> ORGANISM: Artificial Sequence
<220> FEATURE:
<223> OTHER INFORMATION: Synthetic Primer

<400> SEQUENCE: 28
gggtgtcgag ggaaaaatag g                                           21

<210> SEQ ID NO 29
<211> LENGTH: 21
<212> TYPE: DNA
<213> ORGANISM: Artificial Sequence
<220> FEATURE:
<223> OTHER INFORMATION: Synthetic Primer

<400> SEQUENCE: 29
cccaccgtgt tcttcgacat t                                           21

<210> SEQ ID NO 30
<211> LENGTH: 22
<212> TYPE: DNA
<213> ORGANISM: Artificial Sequence
<220> FEATURE:
<223> OTHER INFORMATION: Synthetic Primer

<400> SEQUENCE: 30
ggacccgtat gctttaggat ga                                    22

<210> SEQ ID NO 31
<211> LENGTH: 23
<212> TYPE: DNA
<213> ORGANISM: Artificial Sequence
<220> FEATURE:
<223> OTHER INFORMATION: Synthetic Primer

<400> SEQUENCE: 31
tagtccttcc taccccaatt tcc                                   23

<210> SEQ ID NO 32
<211> LENGTH: 21
<212> TYPE: DNA
<213> ORGANISM: Artificial Sequence
<220> FEATURE:
<223> OTHER INFORMATION: Synthetic Primer

<400> SEQUENCE: 32
ttggtcctta gccactcctt c                                     21

<210> SEQ ID NO 33
<211> LENGTH: 19
<212> TYPE: DNA
<213> ORGANISM: Artificial Sequence
<220> FEATURE:
<223> OTHER INFORMATION: Synthetic Primer

<400> SEQUENCE: 33
cacacgctgc cttgtgtct                                        19

<210> SEQ ID NO 34
<211> LENGTH: 19
<212> TYPE: DNA
<213> ORGANISM: Artificial Sequence
<220> FEATURE:
<223> OTHER INFORMATION: Synthetic Primer

<400> SEQUENCE: 34
ggtcagcaaa agcacggtt                                        19

<210> SEQ ID NO 35
<211> LENGTH: 21
<212> TYPE: DNA
<213> ORGANISM: Artificial Sequence
<220> FEATURE:
<223> OTHER INFORMATION: Synthetic Primer

<400> SEQUENCE: 35
accgccgtca tttatcctga g                                     21

<210> SEQ ID NO 36
<211> LENGTH: 23
<212> TYPE: DNA
<213> ORGANISM: Artificial Sequence
<220> FEATURE:
<223> OTHER INFORMATION: Synthetic Primer

<400> SEQUENCE: 36
catctggtgt tccgttttca tca                                   23

<210> SEQ ID NO 37

```
<211> LENGTH: 21
<212> TYPE: DNA
<213> ORGANISM: Artificial Sequence
<220> FEATURE:
<223> OTHER INFORMATION: Synthetic Primer

<400> SEQUENCE: 37
ggacaagctg agcaagattc a                                              21

<210> SEQ ID NO 38
<211> LENGTH: 19
<212> TYPE: DNA
<213> ORGANISM: Artificial Sequence
<220> FEATURE:
<223> OTHER INFORMATION: Synthetic Primer

<400> SEQUENCE: 38
cggagaaggc gtagctgag                                                 19

<210> SEQ ID NO 39
<211> LENGTH: 19
<212> TYPE: DNA
<213> ORGANISM: Artificial Sequence
<220> FEATURE:
<223> OTHER INFORMATION: Synthetic Primer

<400> SEQUENCE: 39
gctcctctta ggggccact                                                 19

<210> SEQ ID NO 40
<211> LENGTH: 19
<212> TYPE: DNA
<213> ORGANISM: Artificial Sequence
<220> FEATURE:
<223> OTHER INFORMATION: Synthetic Primer

<400> SEQUENCE: 40
ccacgtctca ccattgggg                                                 19

<210> SEQ ID NO 41
<211> LENGTH: 19
<212> TYPE: DNA
<213> ORGANISM: Artificial Sequence
<220> FEATURE:
<223> OTHER INFORMATION: Synthetic Primer

<400> SEQUENCE: 41
cgtccacacg cacctacag                                                 19

<210> SEQ ID NO 42
<211> LENGTH: 21
<212> TYPE: DNA
<213> ORGANISM: Artificial Sequence
<220> FEATURE:
<223> OTHER INFORMATION: Synthetic Primer

<400> SEQUENCE: 42
gggggatgag gaatagaggc t                                              21

<210> SEQ ID NO 43
<211> LENGTH: 21
<212> TYPE: DNA
<213> ORGANISM: Artificial Sequence
<220> FEATURE:
<223> OTHER INFORMATION: Synthetic Primer

<400> SEQUENCE: 43
```
gtcccagaca tcagggagta a                                              21

<210> SEQ ID NO 44
<211> LENGTH: 21
<212> TYPE: DNA
<213> ORGANISM: Artificial Sequence
<220> FEATURE:
<223> OTHER INFORMATION: Synthetic Primer

<400> SEQUENCE: 44
tcggatactt cagcgtcagg a                                              21

<210> SEQ ID NO 45
<211> LENGTH: 21
<212> TYPE: DNA
<213> ORGANISM: Artificial Sequence
<220> FEATURE:
<223> OTHER INFORMATION: Synthetic Primer

<400> SEQUENCE: 45
atgtggaccc ctcctgatag t                                              21

<210> SEQ ID NO 46
<211> LENGTH: 21
<212> TYPE: DNA
<213> ORGANISM: Artificial Sequence
<220> FEATURE:
<223> OTHER INFORMATION: Synthetic Primer

<400> SEQUENCE: 46
gcccagtgat ttcagcaaag g                                              21

<210> SEQ ID NO 47
<211> LENGTH: 22
<212> TYPE: DNA
<213> ORGANISM: Artificial Sequence
<220> FEATURE:
<223> OTHER INFORMATION: Synthetic Primer

<400> SEQUENCE: 47
gagctgtttg cagacaaagt tc                                             22

<210> SEQ ID NO 48
<211> LENGTH: 20
<212> TYPE: DNA
<213> ORGANISM: Artificial Sequence
<220> FEATURE:
<223> OTHER INFORMATION: Synthetic Primer

<400> SEQUENCE: 48
ccctggcaca tgaatcctgg                                                20

<210> SEQ ID NO 49
<211> LENGTH: 24
<212> TYPE: DNA
<213> ORGANISM: Artificial Sequence
<220> FEATURE:
<223> OTHER INFORMATION: Synthetic Primer

<400> SEQUENCE: 49
acgtcagctg aagggaaaca aaca                                           24

<210> SEQ ID NO 50
<211> LENGTH: 22
<212> TYPE: DNA

<213> ORGANISM: Artificial Sequence
<220> FEATURE:
<223> OTHER INFORMATION: Synthetic Primer

<400> SEQUENCE: 50
cggttcaggc agctgcactc tt                                          22

<210> SEQ ID NO 51
<211> LENGTH: 22
<212> TYPE: DNA
<213> ORGANISM: Artificial Sequence
<220> FEATURE:
<223> OTHER INFORMATION: Synthetic Primer

<400> SEQUENCE: 51
tggttcccct gaactttact gt                                          22

<210> SEQ ID NO 52
<211> LENGTH: 20
<212> TYPE: DNA
<213> ORGANISM: Artificial Sequence
<220> FEATURE:
<223> OTHER INFORMATION: Synthetic Primer

<400> SEQUENCE: 52
tgggcaccag aggcatgata                                             20

<210> SEQ ID NO 53
<211> LENGTH: 19
<212> TYPE: DNA
<213> ORGANISM: Artificial Sequence
<220> FEATURE:
<223> OTHER INFORMATION: Synthetic Primer

<400> SEQUENCE: 53
ccaggcatct gccacaatg                                              19

<210> SEQ ID NO 54
<211> LENGTH: 21
<212> TYPE: DNA
<213> ORGANISM: Artificial Sequence
<220> FEATURE:
<223> OTHER INFORMATION: Synthetic Primer

<400> SEQUENCE: 54
cactcaagag cttcccagca a                                           21

<210> SEQ ID NO 55
<211> LENGTH: 20
<212> TYPE: DNA
<213> ORGANISM: Artificial Sequence
<220> FEATURE:
<223> OTHER INFORMATION: Synthetic Primer

<400> SEQUENCE: 55
tcgtggggaa atgtgtccag                                             20

<210> SEQ ID NO 56
<211> LENGTH: 18
<212> TYPE: DNA
<213> ORGANISM: Artificial Sequence
<220> FEATURE:
<223> OTHER INFORMATION: Synthetic Primer

<400> SEQUENCE: 56
ctggccgagt tccagcag                                               18

```
<210> SEQ ID NO 57
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 57

Thr Pro Pro Tyr Ala Asp Pro Ser Leu Gln Ala Pro Val Arg
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 58

Ala Ala Ser Val Val Gln Pro Gln Pro Leu Val Val Val Lys
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 59

Asp Pro Tyr Ala Leu Asp Leu Ile Asp Lys
1               5                   10
```